US012779063B2

(12) United States Patent
Ting et al.

(10) Patent No.: US 12,779,063 B2
(45) Date of Patent: Nov. 3, 2026

(54) METHODS FOR CLEANING DENTAL APPLIANCES

(71) Applicant: Align Technology, Inc., San Jose, CA (US)

(72) Inventors: Fred Ting, San Jose, CA (US); Wesly Wong, Cupertino, CA (US); Zijie Zhu, Santa Clara, CA (US); Byong-Ho Park, San Jose, CA (US); Jun Sato, San Jose, CA (US); Bruce Cam, San Jose, CA (US); Yaser Shanjani, Milpitas, CA (US); Hongling Chen, Santa Clara, CA (US); Zhichao Zhang, Walnut Creek, CA (US)

(73) Assignee: Align Technology, Inc., San Jose, CA (US)

( * ) Notice: Subject to any disclaimer, the term of this patent is extended or adjusted under 35 U.S.C. 154(b) by 1097 days.

(21) Appl. No.: 17/750,288

(22) Filed: May 20, 2022

(65) Prior Publication Data

US 2022/0370654 A1 Nov. 24, 2022

Related U.S. Application Data

(60) Provisional application No. 63/191,274, filed on May 20, 2021.

(51) Int. Cl.
*A61L 2/10* (2026.01)
*A61L 2/24* (2006.01)
(Continued)

(52) U.S. Cl.
CPC .................................... *A61L 2/10* (2013.01); *A61L 2/24* (2013.01); *A61L 2103/05* (2026.01); *A61L 2103/15* (2026.01)

(58) Field of Classification Search
CPC ...... A61L 2/0047; A61L 2/24; A61L 2202/24; A61L 2/025; A61L 2/18; A61L 2202/122;
(Continued)

(56) References Cited

U.S. PATENT DOCUMENTS 5,820,368 A 10/1998 Wolk
5,975,893 A 11/1999 Chishti et al.
(Continued)

FOREIGN PATENT DOCUMENTS

CN 110025796 A 7/2019
CN 111120977 A * 5/2020 .............. A61L 2/10
(Continued)

OTHER PUBLICATIONS

CN-111120977 A1 translation (Year: 2025).*
(Continued)

*Primary Examiner* — Huy Tram Nguyen
(74) *Attorney, Agent, or Firm* — Shay Glenn LLP

(57) ABSTRACT

Methods of cleaning dental appliances. One or more dental appliances may be placed on a frame in a chamber of a cleaning case. The frame may have a planar shape with openings and may be in direct contact with a bottom reflective surface of the chamber. The frame may elevate the one or more dental appliances from the bottom reflective surface to create a gap between the one or more dental appliances and the bottom reflective surface. Activating the cleaning cycle may include: emitting visible light between 400-470 nm from one or more visible light emitting light sources within the closed chamber; and reflecting light from one or more surfaces of the closed chamber, including the reflective bottom surface, to illuminate the one or more dental appliances within the chamber with the 400-470 nm light.

30 Claims, 14 Drawing Sheets

(51) Int. Cl.
*A61L 103/05* (2026.01)
*A61L 103/15* (2026.01)

(58) Field of Classification Search
CPC .... A61L 2202/14; A61L 2202/16; A61L 2/26; A61L 2/10; A61C 17/036
USPC .......................................................... 422/618
See application file for complete search history.

(56) References Cited

U.S. PATENT DOCUMENTS 6,183,248 B1 2/2001 Chishti et al.
6,309,215 B1 10/2001 Phan et al.
6,386,864 B1 5/2002 Kuo
6,450,807 B1 9/2002 Chishti et al.
6,454,565 B2 9/2002 Phan et al.
6,471,511 B1 10/2002 Chishti et al.
6,524,101 B1 2/2003 Phan et al.
6,572,372 B1 6/2003 Phan et al.
6,607,382 B1 8/2003 Kuo et al.
6,705,863 B2 3/2004 Phan et al.
6,783,604 B2 8/2004 Tricca
6,790,035 B2 9/2004 Tricca et al.
6,814,574 B2 11/2004 Abolfathi et al.
6,830,450 B2 12/2004 Knopp et al.
6,947,038 B1 9/2005 Anh et al.
7,074,039 B2 7/2006 Kopelman et al.
7,104,792 B2 9/2006 Taub et al.
7,121,825 B2 10/2006 Chishti et al.
7,160,107 B2 1/2007 Kopelman et al.
7,192,273 B2 3/2007 McSurdy, Jr.
7,347,668 B2 3/2008 Pedersen
7,354,270 B2 4/2008 Abolfathi et al.
7,448,514 B2 11/2008 Wen
7,481,121 B1 1/2009 Cao
7,543,511 B2 6/2009 Kimura et al.
7,553,157 B2 6/2009 Abolfathi et al.
7,600,999 B2 10/2009 Knopp
7,658,610 B2 2/2010 Knopp
7,766,658 B2 8/2010 Tricca et al.
7,771,195 B2 8/2010 Knopp et al.
7,854,609 B2 12/2010 Chen et al.
7,871,269 B2 1/2011 Wu et al.
7,878,801 B2 2/2011 Abolfathi et al.
7,878,805 B2 2/2011 Moss et al.
7,883,334 B2 2/2011 Li et al.
7,914,283 B2 3/2011 Kuo
7,947,508 B2 5/2011 Tricca et al.
8,152,518 B2 4/2012 Kuo
8,172,569 B2 5/2012 Matty et al.
8,235,715 B2 8/2012 Kuo
8,292,617 B2 10/2012 Brandt et al.
8,337,199 B2 12/2012 Wen
8,401,686 B2 3/2013 Moss et al.
8,517,726 B2 8/2013 Kakavand et al.
8,562,337 B2 10/2013 Kuo et al.
8,641,414 B2 2/2014 Borovinskih et al.
8,684,729 B2 4/2014 Wen
8,708,697 B2 4/2014 Li et al.
8,758,009 B2 6/2014 Chen et al.
8,771,149 B2 7/2014 Rahman et al.
8,841,632 B1 9/2014 Griffin et al.
8,899,976 B2 12/2014 Chen et al.
8,899,977 B2 12/2014 Cao et al.
8,936,463 B2 1/2015 Mason et al.
8,936,464 B2 1/2015 Kopelman
9,022,781 B2 5/2015 Kuo et al.
9,119,691 B2 9/2015 Namiranian et al.
9,161,823 B2 10/2015 Morton et al.
9,241,774 B2 1/2016 Li et al.
9,326,831 B2 5/2016 Cheang
9,433,476 B2 9/2016 Khardekar et al.
9,610,141 B2 4/2017 Kopelman et al.
9,655,691 B2 5/2017 Li et al.
9,675,427 B2 6/2017 Kopelman
9,700,385 B2 7/2017 Webber
9,744,001 B2 8/2017 Choi et al.
9,844,424 B2 12/2017 Wu et al.
10,045,835 B2 8/2018 Boronkay et al.
10,111,730 B2 10/2018 Webber et al.
10,150,244 B2 12/2018 Sato et al.
10,201,409 B2 2/2019 Mason et al.
10,213,277 B2 2/2019 Webber et al.
10,299,894 B2 5/2019 Tanugula et al.
10,363,116 B2 7/2019 Boronkay
10,383,705 B2 8/2019 Shanjani et al.
D865,180 S 10/2019 Bauer et al.
10,449,016 B2 10/2019 Kimura et al.
10,463,452 B2 11/2019 Matov et al.
10,470,847 B2 11/2019 Shanjani et al.
10,492,888 B2 12/2019 Chen et al.
10,517,701 B2 12/2019 Boronkay
10,537,406 B2 1/2020 Wu et al.
10,537,463 B2 1/2020 Kopelman
10,548,700 B2 2/2020 Fernie
10,555,792 B2 2/2020 Kopelman et al.
10,588,776 B2 3/2020 Cam et al.
10,613,515 B2 4/2020 Cramer et al.
10,639,134 B2 5/2020 Shanjani et al.
10,743,964 B2 8/2020 Wu et al.
10,758,323 B2 9/2020 Kopelman
10,781,274 B2 9/2020 Liska et al.
10,813,720 B2 10/2020 Grove et al.
10,874,483 B2 12/2020 Boronkay
10,881,487 B2 1/2021 Cam et al.
10,912,629 B2 2/2021 Tanugula et al.
10,959,810 B2 3/2021 Li et al.
10,993,783 B2 5/2021 Wu et al.
11,026,768 B2 6/2021 Moss et al.
11,026,831 B2 6/2021 Kuo
11,045,282 B2 6/2021 Kopelman et al.
11,045,283 B2 6/2021 Riley et al.
11,103,330 B2 8/2021 Webber et al.
11,123,156 B2 9/2021 Cam et al.
11,154,382 B2 10/2021 Kopelman et al.
11,166,788 B2 11/2021 Webber
11,174,338 B2 11/2021 Liska et al.
11,219,506 B2 1/2022 Shanjani et al.
11,259,896 B2 3/2022 Matov et al.
11,273,011 B2 3/2022 Shanjani et al.
11,278,375 B2 3/2022 Wang et al.
11,318,667 B2 5/2022 Mojdeh et al.
11,331,166 B2 5/2022 Morton et al.
11,344,385 B2 5/2022 Morton et al.
11,376,101 B2 7/2022 Sato et al.
2002/0192617 A1 12/2002 Phan et al.
2004/0166462 A1 8/2004 Phan et al.
2004/0166463 A1 8/2004 Wen et al.
2005/0014105 A1 1/2005 Abolfathi et al.
2005/0186524 A1 8/2005 Abolfathi et al.
2005/0244768 A1 11/2005 Taub et al.
2006/0019218 A1 1/2006 Kuo
2006/0078841 A1 4/2006 DeSimone et al.
2006/0115782 A1 6/2006 Li et al.
2006/0115785 A1 6/2006 Li et al.
2006/0199142 A1 9/2006 Liu et al.
2006/0234179 A1 10/2006 Wen et al.
2008/0118882 A1 5/2008 Su
2008/0160473 A1 7/2008 Li et al.
2008/0286716 A1 11/2008 Sherwood
2008/0286717 A1 11/2008 Sherwood
2009/0280450 A1 11/2009 Kuo
2010/0055635 A1 3/2010 Kakavand
2010/0129763 A1 5/2010 Kuo
2010/0269852 A1 * 10/2010 Palfy .................... A61C 17/036 134/1
2010/0326484 A1 12/2010 Wu
2011/0020175 A1 1/2011 Collard et al.
2011/0269092 A1 11/2011 Kuo et al.
2014/0067334 A1 3/2014 Kuo
2015/0265376 A1 9/2015 Kopelman
2015/0366638 A1 12/2015 Kopelman et al.
2016/0193014 A1 7/2016 Morton et al.
2017/0007359 A1 1/2017 Kopelman et al.

(56) References Cited

U.S. PATENT DOCUMENTS

| | | | |
|---|---|---|---|
| 2017/0007360 | A1 | 1/2017 | Kopelman et al. |
| 2017/0007361 | A1 | 1/2017 | Boronkay et al. |
| 2017/0007366 | A1 | 1/2017 | Kopelman et al. |
| 2017/0007386 | A1 | 1/2017 | Mason et al. |
| 2017/0135792 | A1 | 5/2017 | Webber |
| 2017/0135793 | A1 | 5/2017 | Webber et al. |
| 2017/0165032 | A1 | 6/2017 | Webber et al. |
| 2018/0360567 | A1 | 12/2018 | Xue et al. |
| 2019/0000592 | A1 | 1/2019 | Cam et al. |
| 2019/0000593 | A1 | 1/2019 | Cam et al. |
| 2019/0021817 | A1 | 1/2019 | Sato et al. |
| 2019/0046297 | A1 | 2/2019 | Kopelman et al. |
| 2019/0099129 | A1 | 4/2019 | Kopelman et al. |
| 2019/0125494 | A1 | 5/2019 | Li et al. |
| 2019/0125497 | A1 | 5/2019 | Derakhshan et al. |
| 2019/0152152 | A1 | 5/2019 | O'Leary et al. |
| 2019/0167827 | A1 | 6/2019 | Gaska et al. |
| 2019/0175304 | A1 | 6/2019 | Morton et al. |
| 2019/0262101 | A1 | 8/2019 | Shanjani et al. |
| 2019/0298494 | A1 | 10/2019 | Webber et al. |
| 2019/0314119 | A1 | 10/2019 | Kopelman et al. |
| 2019/0343606 | A1 | 11/2019 | Wu et al. |
| 2020/0000553 | A1 | 1/2020 | Makarenkova et al. |
| 2020/0100864 | A1 | 4/2020 | Wang et al. |
| 2020/0100865 | A1 | 4/2020 | Wang et al. |
| 2020/0100866 | A1 | 4/2020 | Medvinskaya et al. |
| 2020/0155276 | A1 | 5/2020 | Cam et al. |
| 2020/0188062 | A1 | 6/2020 | Kopelman et al. |
| 2020/0214598 | A1 | 7/2020 | Li et al. |
| 2020/0214801 | A1 | 7/2020 | Wang et al. |
| 2020/0222568 | A1 | 7/2020 | Lucio |
| 2020/0390523 | A1 | 12/2020 | Sato et al. |
| 2021/0078357 | A1 | 3/2021 | Venkatasanthanam et al. |
| 2021/0147672 | A1 | 5/2021 | Cole et al. |

FOREIGN PATENT DOCUMENTS

| | | | |
|---|---|---|---|
| CN | 211797000 | U | 10/2020 |
| CN | 212792167 | U | 3/2021 |
| KR | 20170106845 | A | 9/2017 |

OTHER PUBLICATIONS

Malayeri et al.; Fluence (UV Dose) required to achieve incremental log inactivation of bacteria, protozoa, viruses and algae; 41 pages; retrieved from the internet (https://uvsolutionsmag.com/stories/pdf/archives/180301_UVSensitivityReview_full.pdf) on May 23, 2022.

Pit et al.; Ultrasound increases the rate of bacterial cell growth Biotechnology Progress; 19(3); pp. 1038-1044; 15 pages; (Author Manuscript); 2003 (the year of publication is sufficiently earlier than the effective U.S. filing date and any foreign priority date so that the particular month of publication is not in issue).

Wang et al.; Antimicrobial blue light inactivation of pathogenic microbes: state of the art; Drug Resistance Updates; 33-35; pp. 1-22; doi:10.1016/j.drup.2017.10.002; 56 pages; (Author Manuscript); Nov. 2017.

* cited by examiner

Light "On"

Light "Off"

METHODS FOR CLEANING DENTAL APPLIANCES

CLAIM OF PRIORITY

This patent application claims priority to U.S. Provisional Patent Application No. 63/191,274, titled "DISINFECTANT DEVICE CASES FOR INTRAORAL APPLIANCES," filed on May 20, 2021, herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Orthodontic procedures typically involve repositioning a patient's teeth to a desired arrangement in order to correct malocclusions and/or improve aesthetics. To achieve these objectives, orthodontic appliances such as braces, shell aligners, and the like can be applied to the patient's teeth by an orthodontic practitioner. The appliance can be configured to exert force on one or more teeth in order to effect desired tooth movements according to a treatment plan.

During orthodontic treatment with patient-removable appliances, the user (e.g., patient) typically removes and reinserts the appliances themselves. What is needed is a device that can permit quick and effective disinfection of one or more orthodontic appliance. It would be preferred for such a tool or device to be configured so that orthodontic appliances, such as aligners and/or palatal expanders, including a series of orthodontic appliances can be quickly and effectively disinfected so that bacteria will not be introduced into a human body during a subsequent use of the appliance.

SUMMARY OF THE DISCLOSURE

Described herein are apparatuses, including devices, tools and systems, including in particular cases for one or more orthodontic appliances, and methods for using them.

For example, described herein are cases for cleaning (e.g., sanitizing and/or sterilizing) one or more orthodontic appliances including (but not limited to) aligners. These cases are configured to be used by the patient and may be portable (e.g., battery powered and/or rechargeable), lightweight (e.g., 700 g or less, 600 g or less, 500 g or less, 450 g or less, 400 g or less, 300 g or less, 250 g or less, 200 g or less, etc.), and/or small (e.g., less than 10 cm×15 cm×10 cm, less than 8 cm×12 cm×8 cm, less than 8 cm×5 cm×8 cm, etc.).

The apparatuses described herein may use one or more cleaning (sanitizing and/or sterilizing) modalities within the case. For example, described herein are apparatuses that use UV light, and in particular, UVC light and/or visible (e.g., blue) light to sanitize and/or sterilize the one or more appliances held within the case. For example, any of these apparatuses may be configured to apply UVC (e.g., wavelengths between about 200-300 nm, such as between 220-280 nm, between 260-280 nm, etc.) either exclusively or in addition to one or more additional portion of the UV spectrum. For example, in some examples more than 50% (e.g., 55% or more, 60% or more 65% or more, 70% or more, 75% or more, 80% or more, 85% or more, 90% or more, 95% or more, etc.) of the applied UV light is UVC. In any of these apparatus, visible light may additionally or alternatively be applied, including light between about 400 and 470 nm. In general, light may be delivered at an intensity and/or duration to inhibit, kill, inactivate, and/or sterilize a pathogen (e.g., bacteria, virus, etc.). For example, when blue light is use, the light-emitting light source may emit light at between 400-470 nm at 10 $J/cm^2$ or more (e.g., 15 $J/cm^2$ or more, 20 $J/cm^2$ or more, 25 $J/cm^2$ or more, 30 $J/cm^2$ or more, 35 $J/cm^2$ or more, 40 $J/cm^2$ or more, 45 $J/cm^2$ or more, 50 $J/cm^2$ or more, 60 $J/cm^2$ or more, 70 $J/cm^2$ or more, 80 $J/cm^2$ or more, 90 $J/cm^2$ or more, 100 $J/cm^2$ or more, etc.).

Any of these apparatuses may include an inner chamber in which the one or more aligners may sit. In some cases, the chamber may be configured to reflect the light (e.g., the UVC light, blue light, etc.). The apparatus may include one or more (e.g., two or more, three or more, etc.) light-emitting light sources within the chamber. For example, in some examples, the chamber may include three or more UVC light sources within the chamber, and/or 3 or more blue-light light emitting LEDs, etc. At least one light-emitting light source may be present on the inside of the lid. In some examples, at least one light source may be present on a sidewall. The device may include a processor (e.g., microprocessor) configured to cycle through a process time that is less than 15 minutes (e.g., 12 minutes or less, 10 minutes or less, 9 minutes or less, 8 minutes or less, 7 minutes or less, 6 minutes or less, 5 minutes or less, 4 minutes or less, etc.). In some examples described herein the cycle time may kill more than 99.5% (more than 99.6%, 99.7%, 99.8%, 99.9%, 99.95%, etc.) of bacteria on the orthodontic appliance.

The apparatus may include a safety interlock that prevent the device from opening while a UV light is on. For example, in some examples the apparatus may include a magnetic lock that prevents the device from opening to expose the inner chamber with the UV light is on; alternatively, the apparatus may include one or more sensors (e.g., a magnetic sensor) that turns the UV light off when the device is opened. For example, a magnetic sensor may detect when the lid is opened and prevent the UV light from turning on and/or turn off the UV light. In some examples, the sensor is on the hinge of the apparatus and/or on a lock portion of the apparatus. The apparatus may include an indicator light that indicates that the device is sanitizing/sterilizing the one or more aligners. For example, a light on the outer surface of the lid may illuminate when UV light is being applied within the device. In any of these apparatuses an alert may be provided once the cycle (e.g., the sanitization/sterilization cycle) is completed, such as one or more of: a light, a tone/beep, a vibration, etc.).

In some examples, the apparatus is rechargeable. For example, the apparatus may include a charging port (e.g., USB-C) and/or cable for charging an internal battery within the apparatus.

As mentioned, the inner surface(s) of the chamber holding the aligner may be reflective, in order to reflect light (e.g., UVC) light. In particular, the top of the chamber (in the lid portion) and/or the bottom of the chamber may be coated with a reflective material, including Aluminum. Reflective aluminum is reflective of UV light, particularly as compared to other materials.

Any of the apparatuses (e.g., appliance cases) described herein may be latching and/or locking when closed. As mentioned, in some examples the apparatus is configured to lock or latch when active (e.g., when the control circuitry/ microcontroller indicates that the apparatus is active, including examples in which the apparatus is applying UV light within the apparatus. For example, the apparatus may be configured to include a snap force applied when opening/closing the apparatus cover. The latching and/or locking configuration may prevent the apparatus from inadvertently opening, e.g., when dropped.

In some examples the apparatuses (e.g., appliance cases) described herein may be configured to position of one or more aligners within the chamber of the apparatus in a position to maximize exposure to the sanitizing and/or sterilizing agent, such as (but not limited to) UV light. For example, in some of the apparatuses described herein, the position of the appliance(s) within the apparatus (e.g., case) is maximized so that the reflective surface(s) within the apparatus direct the sanitizing/sterilizing medium on or into the appliance held therein. For example, when the sanitizing/sterilizing medium includes UV light (e.g., UVC light), the apparatus may be configured to distribute the UVC light within the case evenly or sufficiently evenly so that both outer and inner (e.g., tooth-engaging) surface of the appliance may be receive the UVC light when held within the appliance.

In examples including UV light sources, any appropriate number of UV light sources may be used. For example, in some cases, a single UV light source (e.g., UV-LED, such as a UVC-LED) may be use and may be positioned, e.g., within a center region of the inner chamber (e.g., near a center region of the lid of the chamber). Alternatively or additionally, the apparatus may be configured to so that multiple LEDs (e.g., 2 LEDs, 3 LEDs, 4 LEDs, 5 LEDs, etc.) may be used. In some examples, three LEDs, such as three UVC-emitting LEDs may be used within the apparatus to achieve near-uniform distribution of the light energy within the case. As describe herein ins some examples three UVC-emitting LEDs may be used and may kill more than 99.5% of the bacteria after a 5-minute exposure.

In some of the examples described herein the apparatus may use one or more (e.g., 3, 4, 5, etc.) stationary LEDs to apply sanitization/sterilization energy. In some examples one or more of the LEDs (e.g., UVC-LEDs) applying the sanitization/sterilization energy may be configured to move within the chamber so as to illuminate the target appliance within the chamber from multiple different angles.

The apparatuses described herein may include a controller including or coupled to a power regulating circuitry that may control the power applied to the one or more sanitization/sterilization energy applicators, such as in some examples, one or more LEDs (e.g., UVC-LEDs). The power regulating circuitry may include the power interrupt that may prevent power from being applied when the case is opened, as mentioned above. In some examples the power regulating circuitry may control charging and/or may indicate when a charge is needed (e.g., by light, tone, etc.) or other alert to the user. In examples using one or more LEDs for the sanitization/sterilization energy application, the power regulating (or power control) circuitry may include amplification, such as electrical amplification circuitry in hardware, firmware and/or software that can control the amplification from a power source (e.g., battery) to the apparatus.

In examples in which light, such as UV (e.g., UVC) light is applied for sanitization/sterilization, the lights may be applied continuously during the treatment cycle or they may be pulsed (e.g., turned on/off at some treatment frequency). In some examples where multiple LEDs may be used to apply sanitization/sterilization energy all of the LEDs may be used concurrently within the chamber of the apparatus. In some examples, each LED source may be illuminated separately and sequentially (which may reduce the instantaneous power needs for the apparatus). Fr example, in some of the apparatuses described herein the light(s) within the apparatus chamber may be pulsed with a predetermined frequency to apply energy during a treatment (sanitization/sterilization treatment) cycle.

In general, the apparatuses described herein may be water (fluid) resistant and/or water (e.g., fluid) proof. The inside chamber of the apparatus may be fluid (e.g., water) resistance and/or fluid (e.g., water) proof. For example, the inner surface(s) of the apparatus may be ultrasonically welded to form a unitary internal chamber including a bottom (e.g., tray) piece that may, in some examples, be reflective to the energy to be applied (such as UV light, e.g., by Al coating). The bottom tray may form a watertight seal. In some examples, any of these apparatuses may include a silicone button on the outside that may maintain the seal. Silicone may be used as a sealing material within the chamber, including a silicone ring between the top (lid) and bottom (base).

Also described herein are apparatuses that may be held on a counter ("countertop device") including one or more chambers. These apparatuses may be larger than those configured as portable.

In some examples the apparatus may include a fluid reservoir, such as a water reservoir or tank. In particular, in some examples the sanitization/sterilization energy may be ultrasonic and may use a fluid material into which the ultrasonic energy is applied. In some examples, the apparatus may include a water tank and an ultrasound transducer for applying ultrasound (e.g., between about 40-45 KHz) to sanitize and/or sterilize an appliance within the apparatus. In some examples the apparatus may also include one or more LEDs (e.g., UVC-LEDs) for applying UV sanitization/sterilization energy in addition to or instead of ultrasonic energy.

Some examples of the apparatuses described herein may include one or more modes. For example, any of these apparatuses may include a first "quick" mode that may sanitize an apparatus within the chamber (or chambers) of the apparatus (e.g., a 30 second-5 min cycle, a 30 sec-4 min cycle, a 30 second-3 min cycle, a 30 second-2 min cycle and less than 5 minute cycle, a less than 4 minute cycle, a less than 3 minute cycle, a less than 2 minute cycle, a less than 1 minute cycle, a less than 30 second cycle, etc.). The apparatus may also or additionally include a longer cycle, such as a sterilization cycle, which may apply energy for 5 minutes or more, e.g., 6 minutes or more, 7 minutes or more 8 minutes or more, 9 minutes or more, 10 minutes or more, 12 minutes or more, 15 minutes or more, etc. In examples including multiple sanitization/sterilization energy modes any of these apparatuses may include modes that are specific to each of the sanitization/sterilization energy modes (e.g., UV, ultrasound, heat, etc.) and/or modes that include all or subsets of these modes (e.g., UV and ultrasound, UV and heat, ultrasound and heat, etc.).

Any of these apparatuses may include one or more controls (e.g., buttons, switches, etc.) on the outside of the apparatus for switching between these modes and/or one or more indicators (e.g., LEDs, lights, displays, etc.) for displaying which mode the apparatus is in and/or a progress indicator for where in a cycle the apparatus is. Ins some cases the one or more controls may include an "on," "standby," "active," and/or "off" mode.

The apparatuses may be formed of plastic (polymer), metal, and/or the like. For example, some of these apparatuses may be formed of a polymeric material and/or stainless steel. In some examples the tray (bottom holding surface) may be formed of a stainless steel material. In some examples the top (inner cover surface) may be formed of a stainless steel material.

As mentioned, in some examples the apparatus may include a tank or reservoir of a fluid, such as water and/or a waste tank for receiving used fluid. The fluid may be, e.g., a cleaning fluid, and/or a flavored fluid, etc. For example, the fluid may be flavored with a flavor such as a citrus flavor, a mint flavor, a bubblegum flavor, etc.

The apparatuses (e.g., devices, systems, and the like, including cases) are designed to sterilize one or more dental appliances (e.g., aligners, retainers, night guards, mouth guards, and/or palatal expander). These apparatuses may include one or multiple cleaning methods, such as UVC light, high temperature, ultrasonic vibration, and cleaning chemicals, which may be used sequentially or concurrently. In some examples, the apparatuses may be configured to be portable (e.g., compact, battery-powered, etc.). In some examples the apparatuses may be configured to be plugged into to a wall source of power.

As used herein “cleaning” may include sanitizing, disinfecting, sterilizing, and inactivation (e.g., inactivation of pathogen, such as bacteria, virus, etc.). The term cleaning or cleaner is intended to broadly include removal and/or inactivation of an undesirable material Cleaning may include, but is not limited to, sanitizing, which is the reduction or elimination of pathogenic agents (such as bacteria) from the surfaces of the dental appliance. Unless the context indicates otherwise, cleaning does not require fully sterilizing, although in any of these apparatuses and methods cleaning may refer to sterilization. Thus, the apparatuses described herein may be configured for light cleaning, sanitizing, inactivating pathogens, removing pathogens and/or sterilizing. Except as made clear by the context, an apparatus for sanitizing and/or sterilizing dental appliances may more generally be referred to as an apparatus for cleaning dental appliances.

For example, described herein are apparatuses for cleaning (in some examples for sanitizing and/or sterilizing) one or more dental appliances. Any of these apparatus may include: a housing comprising a lid and a base, wherein the lid is hinged to the base; a chamber formed between the lid and the base within the housing configured to hold two or more dental appliances; one or more ultraviolet light emitting diodes (LEDs) configured to emit ultraviolet light between 200-300 nm (UVC) within the closed chamber; a UVC-reflective surface of the base forming a bottom of the chamber; and a controller configured to control the power the one or more ultraviolet LEDs so that they are powered only when the chamber is closed in order to clean (e.g., sanitize and/or sterilize) the one or more dental appliances within the chamber.

The housing may comprise a clamshell housing. The housing may be configured to be handheld.

Any of these apparatuses may include a UVC-reflective aluminum surface on a top surface of the chamber formed in the lid. The UVC-reflective surface may be any appropriate UV reflective surface, including but not limited to an aluminum surface. The one or more UVC LEDs may include a plurality of UVC LEDS on a top surface of the chamber formed by the lid.

Any of these apparatuses may include a sensor configured to detect an open and/or closed state of the chamber.

The controller may be configured to receive input from the sensor and to disable power to the one or more LEDs when the chamber is open.

In general, these apparatuses may include one or more controls on an outer surface of the housing. The one or more controls may include a mode selection control configured to select between a sanitizing mode and a sterilizing mode.

Any of these apparatuses may include one or more ultrasound transducer configured to deliver ultrasound energy to the chamber. The ultrasound emitter may be configured to emit ultrasound of between about 40-45 KHz.

The apparatuses described herein may include a fluid reservoir within the housing and configured to hold a fluid, wherein the fluid reservoir is configured to be in communication with the chamber to deliver fluid into the chamber.

Any of these apparatuses may include a waste reservoir within the housing configured to receive fluid from the chamber.

These apparatuses may also or alternatively include a frame within the chamber configured to hold the two or more dental appliances above the UVC-reflective surface of the bottom of the chamber.

The frame may be removable.

In some cases, the bottom of the chamber nay be configured to rotate. The one or more LEDs may be configured to move relative to an appliance within the chamber.

The apparatus may include one or more light pipes within the chamber configure to emit UVC light. Thus, the light pipe may direct the light to any region, including within the tooth-receiving region of an aligner.

In general, the apparatus may include one or more ultraviolet sensors configured to detect UV light within the chamber.

The controller may be configured to scan a dental appliance within the chamber using one or more adjustable mirrors.

For example, described herein are apparatuses for sanitizing and/or sterilizing one or more dental appliances, the apparatus comprising: a clamshell housing comprising a lid and a base, wherein the lid is hinged to the base; a chamber formed between the lid and the base within the clamshell housing configured to hold two or more dental appliances; a plurality of ultraviolet light emitting diodes (LEDs) configured to emit ultraviolet light between 200-300 nm (UVC) within the closed chamber; a UVC-reflective aluminum surface on an inner face of the lid within the chamber, and on a bottom of the chamber; a sensor configured to detect the open or closed state of the chamber; and a controller receiving input from the sensor and configured to control the power the plurality of ultraviolet LEDs so that they are powered only when the chamber is closed in order to sanitize and/or sterilize the dental/orthodontic appliance within the chamber.

In any of these apparatuses the plurality of UVC LEDs may include a plurality of UVC LEDS on a top surface of the chamber formed by the lid. The controller may be configured to receive input from the sensor and to disable power to the one or more LEDs when the chamber is open. As mentioned, the apparatus may include one or more controls on an outer surface of the housing; for example, the one or more controls may comprise a mode selection control configured to select between a sanitizing mode and a sterilizing mode.

In some examples, described herein are apparatuses for sanitizing and/or sterilizing one or more dental appliances that include: a housing comprising a lid and a base, wherein the lid is hinged to the base; a chamber formed between the lid and the base within the clamshell housing configured to hold two or more dental appliances; a fluid reservoir within the housing and configured to hold a fluid; a waste reservoir within the housing configured to receive fluid from the chamber; an ultrasound transducer configured to deliver ultrasound energy to the chamber; a one or more ultraviolet light emitting diodes (LEDs) configured to emit ultraviolet light between 200-300 nm (UVC) within the closed chamber; a UVC-reflective aluminum surface on a bottom of the chamber; and a controller configured to control the power the ultrasound transducer and to the one or more ultraviolet LEDs so that the one or more ultraviolet LEDs are powered only when the chamber is closed in order to sanitize and/or sterilize the dental/orthodontic appliance within the chamber. As mentioned, the ultrasound emitter may be configured to emit ultrasound of between about 40-45 KHz. The one or more UVC LEDs may comprise a plurality of UVC LEDS on a top surface of the chamber formed by the lid.

Any of these apparatuses may include a sensor configured to detect an open and/or closed state of the chamber. The controller may be configured to receive input from the sensor and to disable power to the one or more LEDs when the chamber is open.

Also described herein are methods, including methods of sanitizing and/or sterilizing one or more dental appliances, that include: inserting one or more dental appliances into a chamber of a cleaning case; closing a lid of the cleaning case; sensing when the lid is closed and activating, while the lid remains closed, a sanitizing and/or sterilizing cycle by a controller of the cleaning case, wherein activating the sanitizing and/or sterilizing cycle comprises: emitting ultraviolet light between 200-300 nm (UVC) from one or more light emitting diodes (LEDs) within the closed chamber; reflecting UVC from a UVC reflective surface on a bottom of the closed chamber to illuminate the one or more dental appliances within the chamber; and deactivating the sanitizing and/or sterilizing cycle when either a timer has counted to a predetermined cycle time or when the lid is opened.

Any of these methods may include activating the sanitizing and/or sterilizing cycle comprises emitting ultrasound from one or more ultrasound transducers into the chamber.

For example, described herein are cleaning apparatuses and methods that use both light and mechanical agitation (e.g., cavitation) by the application of ultrasound. For example an apparatus for cleaning one or more dental appliances may include: a housing comprising a lid and a base, wherein the lid is coupled to the base; a chamber formed between the lid and the base within the housing, wherein the chamber is configured to hold a fluid; one or more light-emitting light sources configured to emit light within the closed chamber and into the fluid within the chamber; an ultrasound transducer configured to deliver ultrasound energy to the chamber; and a controller configured to control the power to the one or more light-emitting light sources and the ultrasound transducer to cause cavitation of a fluid within the chamber while delivering light from the one or more light-emitting light sources in order to clean one or more dental appliance within the chamber. As mentioned above, the one or more light-emitting light sources may be an ultraviolet light between 200-300 nm (UVC) light source. In some examples the one or more light-emitting light sources is a visible-light light source emitting at between 400-470 nm. The one or more light-emitting light sources may emit, e.g., 10 J/cm$^2$ or more. These apparatuses may include any of the apparatus features described herein.

Also described herein are methods of cleaning one or more dental appliances using two or more modalities such as light (UV or visible light) and mechanical energy (e.g., ultrasound induced cavitation). These methods may include: inserting one or more dental appliances into a chamber of a cleaning case including a controller; closing a lid of the cleaning case; and activating, by the controller, a cleaning cycle, wherein activating the cleaning cycle comprises: emitting a light from one or more light-emitting light sources within the closed chamber into a fluid within the chamber, wherein the one or more dental appliances is within the fluid; emitting ultrasound from one or more ultrasound transducers into the chamber to induce cavitation of the fluid within the chamber.

Although the apparatuses and method described herein may be configured to generate ultrasound without inducing cavitation, it is particularly beneficial to provide cavitation in order to "scrub" the dental appliance surfaces as it is being cleaned. Indeed, although some research has suggested that ultrasound may actually increase pathogen activity at lower energies, ultrasound energies sufficient to generate cavitation within the cleaning solution may provide mechanical cleaning, which may be surprisingly effective when combined with light irradiation as described herein. In any of these methods emitting the light from the one or more light-emitting light sources may comprises emitting an ultraviolet light between 200-300 nm (UVC). Alternatively, emitting the light from the one or more light-emitting light sources may comprises emitting a visible light at between 400-470 nm. Emitting may comprise emitting 10 J/cm$^2$ or more.

Also described herein are apparatus for cleaning one or more dental appliances that include UVC light. These apparatuses may include: a housing comprising a lid and a base, wherein the lid is hinged to the base; a chamber formed between the lid and the base within the housing configured to hold one or more dental appliances; one or more ultraviolet light emitting diodes (LEDs) configured to emit ultraviolet light between 200-300 nm (UVC) within the closed chamber; a UVC-reflective surface of the base forming a bottom of the chamber; and a controller configured to control the power the one or more ultraviolet LEDs so that they are powered only when the chamber is closed in order to clean the one or more dental appliances within the chamber.

Any of the apparatuses described herein may be configured for the application of visible light to clean a dental appliance (e.g. aligner). For example, described herein are apparatuses for cleaning one or more dental appliances, the apparatus comprising: a housing comprising a lid and a base, wherein the lid is coupled to the base; a chamber formed between the lid and the base within the housing configured to hold one or more dental appliances; one or more visible light emitting light sources configured to emit visible light between 400-470 nm within the closed chamber; a reflective surface of the base forming a bottom of the chamber configured to reflect light between 400-470 nm; and a controller configured to control the power the one or more visible light emitting light sources.

These apparatuses may include any of the features described herein. For example, any of these apparatuses may include: one or more ultrasound transducer configured to deliver ultrasound energy to the chamber. The ultrasound emitter may be configured to emit ultrasound of between about 40-45 KHz.

In some examples these apparatuses for cleaning one or more dental appliances may include: a housing comprising a lid and a base, wherein the lid is coupled to the base; a chamber formed between the lid and the base within the housing, wherein the chamber is configured to hold one or more dental appliances within a fluid within the chamber; one or more visible light emitting light sources configured to emit visible light between 400-470 nm within the closed chamber and into the fluid within the chamber; wherein the chamber comprises a reflective surface configured to reflect light between 400-470 nm; an ultrasound transducer configured to deliver ultrasound energy to the chamber; and a controller configured to control the power the one or more visible light emitting light sources and the ultrasound transducer to cause cavitation of a fluid within the chamber while delivering visible light from the one or more visible light emitting light sources.

The one or more visible light emitting light sources may comprise a high-output 400-470 nm LEDs. For example, the controller may be configured to control the power to the one or more visible light emitting light sources to emit 10 $J/cm^2$ or greater. In any of these examples the controller is configured to control the power to the one or more visible light emitting light sources to emit 30 $J/cm^2$ or greater. The one or more visible light emitting light sources may comprise a plurality of high-output blue-light LEDS on a top surface of the chamber formed by the lid.

Any of these apparatuses may include a fluid reservoir in communication with the chamber. Any of these apparatuses may include a waste reservoir within the housing configured to receive fluid from the chamber. The housing may comprise a clamshell housing. The housing may be configured to be handheld. The chamber may comprise a reflective aluminum surface. Any of these apparatuses may include one or more controls on an outer surface of the housing. The one or more controls may comprise a mode selection control configured to select between a sanitizing mode and a sterilizing mode. The apparatus may include a frame within the chamber configured to hold the one or more dental appliances above a bottom of the chamber. The frame may be removable. In any of these apparatuses the bottom of the chamber may be configured to rotate. The one or more visible light emitting light sources may be configured to move relative to an appliance within the chamber.

Also described herein are methods of cleaning using UV light (with or without ultrasound). For example, a method of cleaning one or more dental appliances may include: inserting one or more dental appliances into a chamber of a cleaning case having a controller; closing a lid of the cleaning case; and activating a cleaning cycle, wherein activating the cleaning cycle comprises: emitting visible light between 400-470 nm from one or more visible light emitting light sources within the closed chamber; reflecting light from one or more surfaces of the closed chamber to illuminate the one or more dental appliances within the chamber with the 400-470 nm light.

Any of the methods described herein may include continuing the cleaning cycle until one or more of: a timer has counted to a predetermined cycle time, or a stop command has been received by the controller. For example, continuing the cleaning cycle until the timer has counted to a predetermined cycle time may comprise continuing until the timer has counted to a time that is 3 hours or longer (4 hours or more, 5 hours or more, 6 hours or more, etc.).

In any of these apparatuses and methods the chamber may be filled with liquid prior to starting the cleaning cycle. The chamber may be filled before, during or after inserting the one or more dental appliances (e.g., aligners).

Activating the cleaning cycle may comprise emitting ultrasound from one or more ultrasound transducers into the chamber. As mentioned, in general, emitting ultrasound may include causing cavitation of a fluid within the chamber.

In any of these examples, emitting visible light between 400-470 nm comprises emitting light at 10 $J/cm^2$ or greater (e.g., 15 $J/cm^2$ or greater, 20 $J/cm^2$ or greater, 30 $J/cm^2$ or greater, 40 $J/cm^2$ or greater, etc.).

Any of the methods of cleaning described herein may include heating the chamber during the cleaning cycle. Any of these method of cleaning may include sensing a pathogen or a pathogen byproduct on a dental appliance within the chamber, and in some examples, modifying the cleaning cycle based on the sensed pathogen or pathogen byproduct.

For example, a method of cleaning one or more dental appliances may include: inserting one or more dental appliances into a chamber of a cleaning case including a controller; closing a lid of the cleaning case; and activating, by the controller, a cleaning cycle, wherein activating the cleaning cycle comprises: emitting visible light between 400-470 nm from one or more visible light emitting light sources within the closed chamber into a fluid within the chamber; emitting ultrasound from one or more ultrasound transducers into the chamber to induce cavitation of the fluid within the chamber.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 3A shows a perspective view. FIG. 3B shows a top view with an indicator "on" and FIG. 3C shows the top view with the indicator "off".

DETAILED DESCRIPTION

Figure 1A:
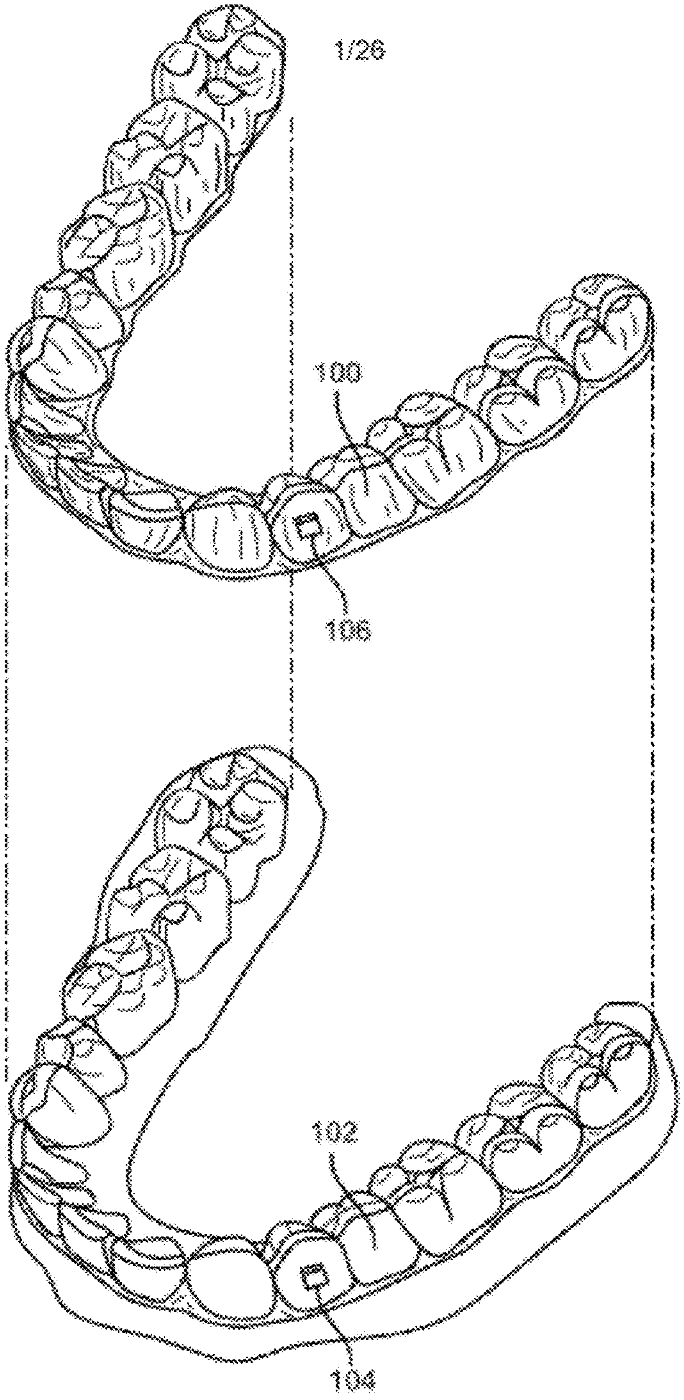
FIG. 1A illustrates an example of a tooth repositioning appliance.

Described herein are apparatuses for sanitizing and/or sterilizing one or more dental appliances, such as dental aligners, palatal expanders, retainers, night guards, and/or mouth guards).

In some examples, these apparatuses are configured for sanitizing and/or sterilizing an aligner, or more than one aligner, including a series of aligners to be worn by a patient as part of a treatment plan to move teeth to desired positions.

Any of the apparatuses described herein may sanitize and/or sterilize by the application of heat (e.g., autoclaving), as will be described in greater detail herein. Any of the apparatuses described herein may sanitize and/or sterilize by the application of ultraviolet light. In particular, these apparatuses may be configured to operate by the application of UVC either exclusively or in addition to one or more additional portion of the UV spectrum. For example, in some examples more than 50% (e.g., 55% or more, 60% or more 65% or more, 70% or more, 75% or more, 80% or more, 85% or more, 90% or more, 95% or more, etc.) of the applied UV light is UVC.

Alternatively or additionally, any of these apparatuses may be configured to detect or indicate contamination of the dental appliance. For example, any of these apparatuses may be configured to indicate bacterial contamination, e.g., by indicating the presence of bacteria. In some examples these apparatuses may indicate odors, such as by including an odor-imaging sensor in the apparatus, which may detect odorants within the apparatus chamber. For example, the sensor may include a sensor substrate, such as quartz crystal microbalance (QCM), as a high-precision mass detector to detect mass changes in resonance frequency at the surface of substrate. The substrate may include thin film (or films) having regions configured to have different chemically affinities (for instance, high/low polarity, hydrophobicity/hydrophilicity, and so on). An odorant may interact with these different regions of the sensor and may result in a change in frequency of the substrate/membrane. The pattern of membrane regions and/or the frequency changes may be characteristic of odors associated with contamination of the dental appliance.

In general, the methods and apparatuses described herein may be used with any appropriate type of dental appliance and may be adapted for use with one or more type of dental appliance. For example, described herein are apparatuses that may be used with dental aligners, and may be configured by shape, size and/or retaining regions, as well as other features described in detail herein, for receiving and sanitizing and/or sterilizing an aligner or multiple aligners.

Thus, the intraoral appliance may be an orthodontic appliance, such as an aligner, used to reposition one or more of the patient's teeth to a desired arrangement, e.g., to correct a malocclusion. Alternatively or additionally, the intraoral appliance may be used to maintain one or more of the patient's teeth in a current arrangement, such as a retainer. Other examples of intraoral appliances suitable for use in conjunction with the embodiments herein include sleep apnea treatment devices (e.g., mandibular advancement devices or splints), night guards (e.g., for treating bruxism), mouth guards, and palatal expanders.

Appliances having teeth receiving cavities that receive and reposition teeth, e.g., via application of force due to appliance resiliency, are generally illustrated with regard to FIG. 1A. FIG. 1A illustrates an exemplary tooth repositioning appliance or aligner 100 that can be worn by a patient in order to achieve an incremental repositioning of individual teeth 102 in the jaw. The appliance can include a shell having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication (e.g., 3D printing, additive manufacturing), for example. Alternatively or in combination, the appliance can be fabricated with machining such as an appliance fabricated from a block of material with computer numeric control machining.

An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth) and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some embodiments, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 104 on teeth 102 with corresponding receptacles or apertures 106 in the appliance 100 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the URL "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Figure 1B:
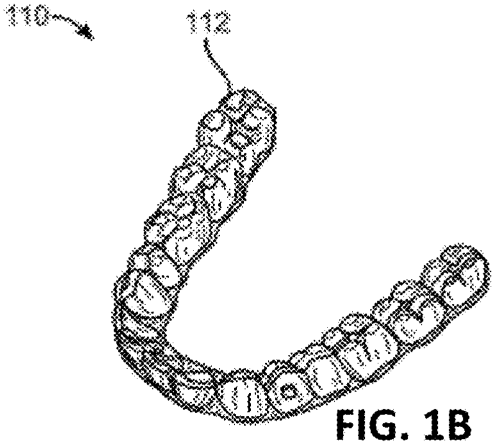
FIGS. 1B-1D shows an example of a tooth repositioning system.
Figure 1C:
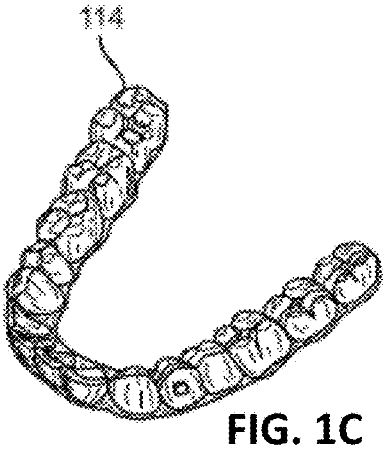
Figure 1D:
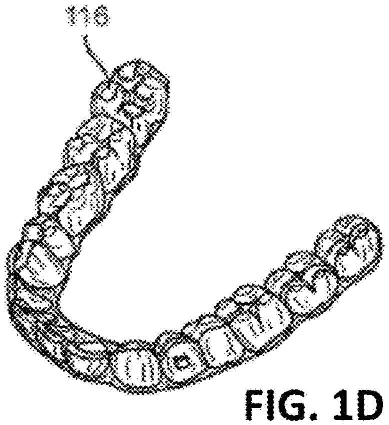

FIGS. 1B-1D illustrate an example of a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

The various embodiments of the orthodontic appliances presented herein can be fabricated in a wide variety of ways. As an example, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell. Alternatively or in combination, some embodiments of the appliances herein may be directly fabricated, e.g., using rapid prototyping, stereolithography, 3D printing, and the like.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

In some embodiments, orthodontic appliances, such as the appliance illustrated in FIG. 1A, impart forces to the crown of a tooth and/or an attachment positioned on the tooth at one or more points of contact between a tooth receiving cavity of the appliance and received tooth and/or attachment. The magnitude of each of these forces and/or their distribution on the surface of the tooth can determine the type of orthodontic tooth movement which results. Tooth movements may be in any direction in any plane of space and may comprise one or more of rotation or translation along one or more axes. Types of tooth movements include extrusion, intrusion, rotation, tipping, translation, and root movement, and combinations thereof, as discussed further herein. Tooth movement of the crown greater than the movement of the root can be referred to as tipping. Equivalent movement of the crown and root can be referred to as translation. Movement of the root greater than the crown can be referred to as root movement.

For example, described herein are apparatuses that clean (in some cases that sanitize and/or sterilize) one or more dental (or orthodontic) appliances. As used herein sanitizing a dental appliance typically means to make the dental appliance clean and hygienic, so that it is disinfected to a level that is safe for use within the mouth of the patient for whom the appliance is intended to treat. In some examples the apparatuses described herein may sterilize the appliance (s), such as by making it substantially (e.g., completely or nearly completely) free from bacteria or other living microorganism. Sterilizing may get rid of all or nearly all germs, sanitizing may lower the amount to a safe level.

In general, the apparatuses described herein may kill a large spectrum of different pathogens, including in particular, viruses (e.g. COVID-19), bacteria (e.g., *E. coli, S. aureus, P. aeruginosa, S. mutans, P. loesheii*, and *F. nucleatum* and others), and may keep dental appliance hygienic and clean. These apparatuses may kill all or substantially all of these pathogens, and/or may reduce the effective amount of pathogen(s) to a safe level for use within the patient's mouth.

The apparatuses described herein may use one or more (e.g., multiple methods) that can be combined and implemented into the disinfectant apparatuses for dental appliances described herein. In some examples the apparatus applies UV light to disinfect and/or sterilize the appliance(s). UV light may kill or inactivate microorganisms by destroying nucleic acids and disrupting their DNA, leaving them unable to perform vital cellular functions. In particular, the apparatuses described herein may use UV-C, with wavelength between about 200-280 nm (e.g., 260-280 nm, etc.) for disinfection. Within these wavelengths, light can quickly break the molecular bonds that hold bacterial DNA together, which may prevent bacteria from reproducing, so bacteria die off instead of growing and/or dividing. In some examples, the UVC light applied may be centered around about 264 nm.

In some examples, these apparatuses may apply a high temperature to sanitize and/or sterilize the appliances in the apparatuses described herein. For example, a high temperature may be used via medium such as steam. For example, the apparatus may apply steam sterilization, as accomplished in an autoclave, by exposing an appliance to direct steam contact at a required or predetermined temperature and/or pressure for a specified time. For example, the apparatuses described herein may apply a dry saturated steam and entrained water (dryness fraction≥97%). Pressure may serve as a means to obtain the high temperatures useful to quickly kill microorganisms. Specific temperatures may be maintained to eliminate or reduce microbicidal activity. For example, a steam-sterilizing temperature may be between about 121° C. (250° F.) and 132° C. (270° F.). These temperatures (and other high temperatures) must be maintained for a minimal time to kill microorganisms. Minimum exposure periods for sanitization may be between 6 minutes and 60 minutes, depending on the temperature and/or pressure. For example, sterilization of an appliance may be achieved by exposure for 30 minutes or more at 121° C. (250° F.) or 4 minutes at 132° C. (270° F.) in some examples. Generally the exposure may be for between 4-60 minutes at a temperature (steam temperature) of between about 121° C. (250° F.) and 132° C. (270° F.), or greater. In any of these apparatuses and methods flash sterilization/flash sanitization may be used. For example, the apparatus may apply flash steam sterilization (or sanitization) at a temperature of about 132° C. (270° F.) for 3 minutes. This can be performed in a closed container of the apparatus to allow for rapid penetration of steam on the appliance(s) within the apparatuses.

In some examples, either alternatively or additionally, the apparatus may be configured to apply ultrasonic vibration for sanitization and/or sterilization. Ultrasonic cleaning uses ultrasound (e.g., between about 20-40 kHz) to agitate a fluid. The agitation produces high forces on contaminants adhering to substrates such as to the appliance. Contaminants can include dust, dirt, oil, pigments, rust, grease, algae, fungus, bacteria, lime scale, polishing compounds, flux agents, fingerprints, soot wax and mold release agents, biological soil like blood, and so on. The ultrasound can be used with water and/or with a solvent appropriate for the appliance being cleaned and/or the type of soiling present enhances the effect. Cleaning may last between 2-60 minutes (e.g., between 3-30 minutes, between 3-30 minutes, between 2-20 minutes, between 2-15 minutes, between 2-12 minutes, between 2-10 minutes, between 2-8 minutes, between 2-6 minutes, and/or longer. For example, in some examples the cleaning ultrasound may be applied for between 20 minutes or more.

Any of the apparatuses described herein may additionally and/or alternatively use one or more cleaning chemicals. Chemicals may include detergents, antibacterial agents, etc.; in some examples, the cleaning chemicals may be mixing with water. Chemical agents that can remove odor-causing bacteria and keep appliance clean and bright may be particularly useful. For example, cleaning chemicals (cleaning agents) that may be used may include one or more of: Sodium Carbonate, Sodium Sulfate, Sodium Tripolyphosphate, Sodium Dichlorosocyanurate, and/or Sodium Lauryl Sulfate.

Figure 2:
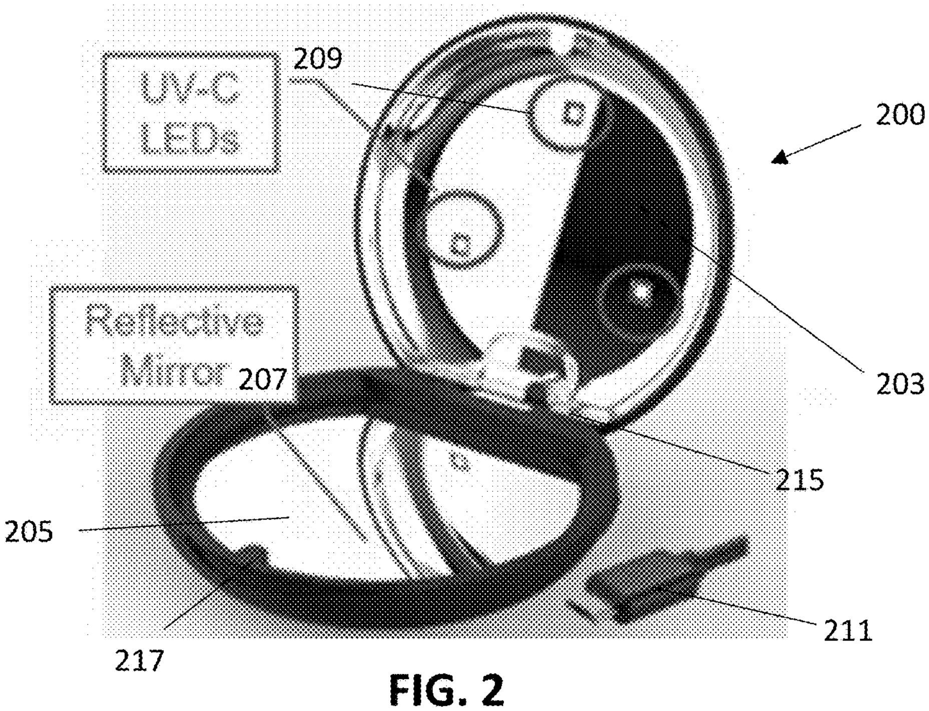
FIG. 2 shows one example of an apparatus for sanitizing and/or sterilizing a dental/orthodontic appliance, configured as a cleaning case.

FIG. 2 illustrates one example of an apparatus for sanitizing and/or sterilizing one or more dental appliances 200 as described herein. In FIG. 2, the apparatus is configured as a clamshell apparatus having an upper lid 203 hinged to a lower base 205 portion forming a chamber therebetween. This inside of this chamber, both the base region 207 and the upper lid region 209 are coated with a reflective Aluminum material forming a UVC-reflective surface 207 as shown. In this example multiple UVC-LEDs are included 209, arranged on the upper lid portion. Alternatively or additionally, the UV (e.g., UVC) LEDs may be positioned on the bottom and/or sides of the inner chamber. The apparatus may also include internal control circuitry (not shown) that may control operation of the application of light from the LEDs to sanitize and/or sterilize, including how long the light is applied for and/or if the energy is applied from all LEDs at the same time or in a pattern and/or frequency. The control circuitry may also determine if the apparatus is closed or opened and may disable the LEDs from operating if the lid is opened. For example, one or more sensors (e.g., magnetic sensors, encoders, etc.) may be included to detect an open/closed (and/or sealed) state of the apparatus. For example, a sensor may be positioned at or in the hinge region(s) 215 and/or in a front latch region 217. Any of these examples may include a latch and/or lock for securing the apparatus in a closed configuration.

Figure 3A:
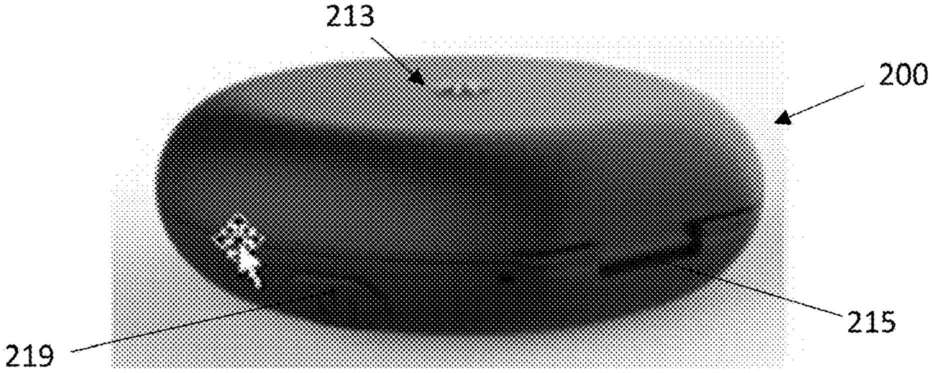
FIGS. 3A-3C show another example of an apparatus for sanitizing and/or sterilizing a dental/orthodontic appliance.
Figure 3B:
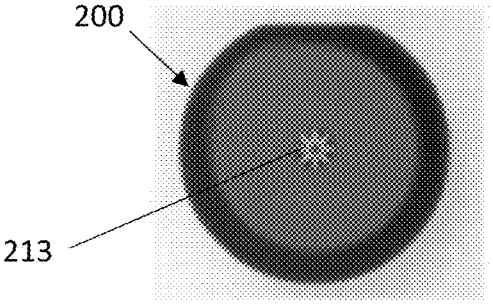
Figure 3C:
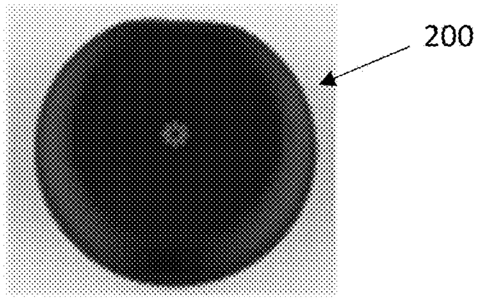

FIGS. 3A-3C show perspective (FIG. 3A) and top views (FIGS. 3B-3C) of an example of an apparatus (configured as a UV-sanitizing/sterilizing case) similar to that shown in FIG. 2. In FIG. 3A the back of the apparatus 200 is shown, including a control (button) 219 that may be used to control the apparatus, including switching between different modes and/or turning the device on/off. The cover of the apparatus may also include one or more LED indicators (outputs) 213. In FIG. 3B the indicator is shown "on" indicating that the device is in use, with the LED(s) illuminating during an operational cycle, while in FIG. 3C the indicator is shown off, indicating that the LED(s) is/are off. The indicator may be configured to indicate one or more states (e.g., operational states, off state, standby state, time left in the cycle, etc.). For example, the indicator LEDs may be configured to illuminate in color. IN some examples multiple LEDs may be used as indicators, including the "petals" of the LEDs arranged in the circle or floral shape shown. As the device cycles through its operation, it may change the number of LEDs illuminated to indicate the remaining time in the treatment (sanitizing/sterilizing) cycle left. The button 219 shown may be used to select the treatment cycle (e.g., a short/quick sanitizing cycle and/or a long sterilizing cycle, etc.) and/or to turn on or off the apparatus. The number of pushing of the button and/or the duration of pushes (or time between pushes) may determine the control input (cycle selection, turn on/off, etc.). FIG. 3C illustrates an example of an apparatus with the device "off" (showing the LED indicator on the lid off).

Any of these apparatuses may include a power supply within the apparatus (e.g., in the base and/or lid, such as beneath the bottom of the chamber in the base and/or above the top of the chamber in the lid. In some examples the apparatus includes one or more rechargeable power supplies (e.g., batteries). The control circuitry may include power regulatory circuitry for regulating the power to/from the battery, including charging the apparatus from a wall power source such as a cable (e.g., USB cable 211). Thus the apparatus may include a USB port for powering and/or controlling the apparatus. In some examples the power circuitry may also or additionally be configured to regulate the power to/from the apparatus for regulating power when the apparatus is applying energy to the LEDs. For example, the controller may modulate the power so that the UV-LEDs (e.g., UVC-LEDs) are powered using a frequency or at a steady-state.

The apparatus shown in FIGS. 2 and 3A-3C may be configured as a portable apparatus. This apparatus may be configured to disinfect (e.g., sterilize and/or sanitize) one or more dental/orthodontic appliances. For example, an apparatus may be configured as a disinfectant device that can be configured as a case for a dental appliance such as an aligner. The apparatus may include one or more UV-emitting LEDs such as multiple UVC-LEDs, that may be positioned on the top, bottom and or sides of the apparatus. In some examples the apparatus includes UV (e.g., UVC) LEDs at the bottom surface of the case and/or the top surface of the inner chamber within the case (as shown in FIG. 2). The apparatus may include a reflective (e.g., UV, such as UVC reflective) mirror that may enhance the efficiency of UV light within the closed chamber. In some examples one or more cleaning chemicals, such as cleaning crystal spray, can facilitate the sterilization process. The portable devices shown in FIGS. 2 and 3A-3B may be configured to provide efficient way to disinfect one or more dental appliances, while keeping the small form factor (only a few millimeters added in height to the current aligner case design). This device is suitable to be put in pocket for daily usage and has rechargeable battery to power the LEDs.

Figure 4:
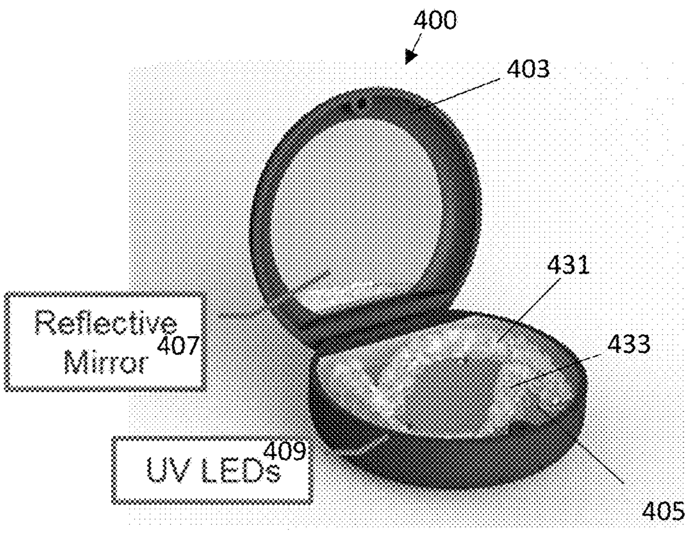
FIG. 4 shows another example of an apparatus for sanitizing and/or sterilizing a dental/orthodontic appliance, including a pair of appliances (e.g., aligners).

FIG. 4 shows another example of a sterilizing and/or sanitizing case for a dental appliance, shown in this example holding a pair of aligners 431, 433. The aligners are held within the chamber of the apparatus 400. In this example the LEDs (e.g., UVC-LEDs) 409 are on the bottom (base 405) of the case. The top (lid portion 403) includes a UV-reflective mirror 407 (e.g., an aluminum coating). The combination of the mirrored surface opposite from the UV-LEDs may provide a uniform light distribution; in some examples, as shown in FIG. 2, the bottom surface and/or sides may also be reflective.

Figure 5:
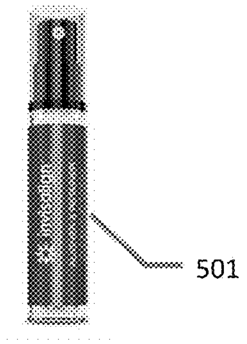
FIG. 5 illustrates one example of a cleaning spray that may be used with any of the appliances described herein.

FIG. 5 illustrates one example of a spray bottle containing a cleaning solution that may be used with any of the apparatuses described herein. The cleaning solution may include a flavor or scent and or an antibacterial/antiviral composition.

The apparatuses described herein may be battery-powered and may include a user interface and one or more controls for operating the apparatus, as mentioned above. For example, the apparatus may include one or more controls for operating the UV LEDs within the case. For example, a control (e.g., a button) on the outside of the case may allow the user to start the disinfection cycle and/or to pick parameters of the cycle (e.g., fast/quick sanitizing or longer sterilization, etc.). This may active the UV LED's (e.g., UVC LEDs) within the case, exposing the contents of the container to UV light for a preset amount of time, and/or at a predetermined frequency and/or intensity (e.g., based on the number of LEDs concurrently illuminated). An indicator on the outside of the case may be illuminated, indicating that the UV LEDs are active during the disinfection timing cycle. When the cycle is complete, the UV LED's may be turned off along with the user indicator. If the case is opened while the UV LEDs are on during the disinfection cycle, the UV LED's may be turned off and the timing cycle may be terminated. In some examples, external control of the UV LED's may be controlled by digital signals from a host source (e.g., three or more digital signals). For example, these signals may allow the host to control each of the UV LEDs independently.

Figure 6:
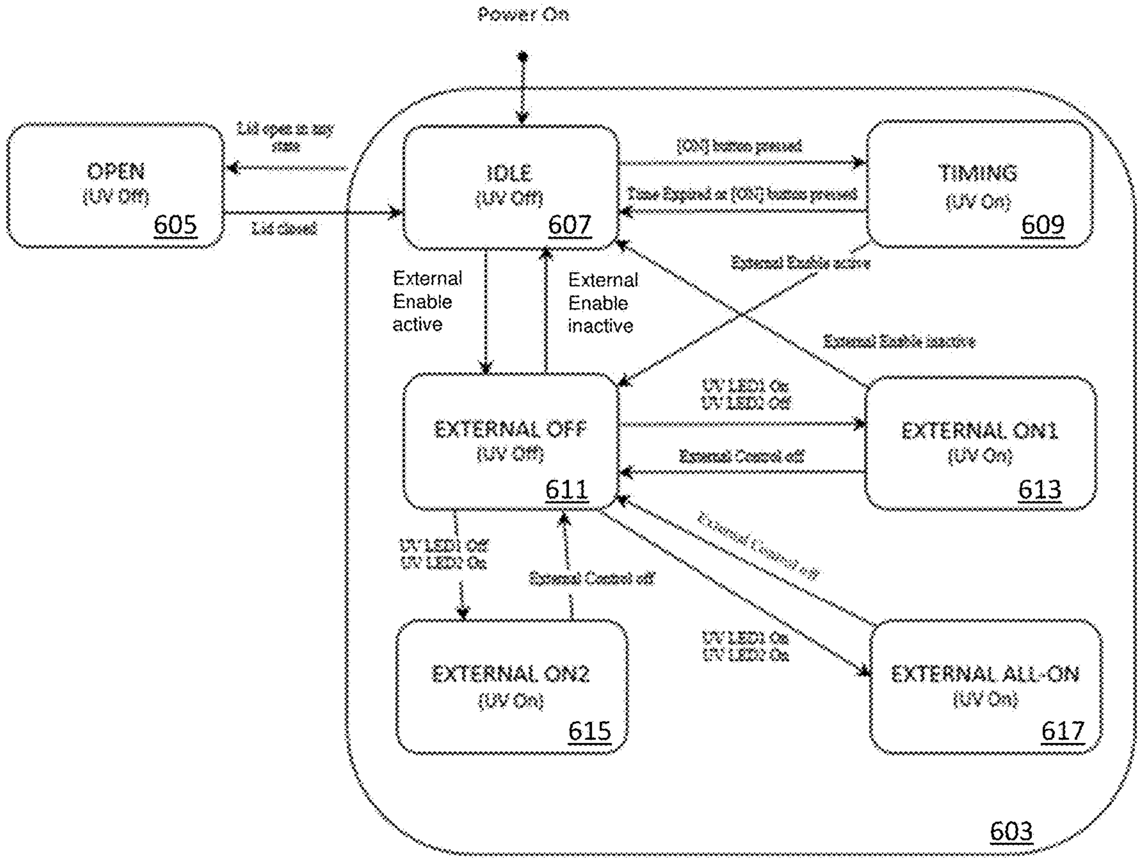
FIG. 6 shows a state diagram for one example of an apparatus for sanitizing and/or sterilizing a dental/orthodontic appliance as described herein.

FIG. 6 shows one example of a state diagram for an apparatus (e.g., configured as a disinfecting case) as described herein. In FIG. 6, the state diagram includes two primary states, "on" 603 when the power is on and the lid is shut, and lid open 605, when the lid is open (causing the UV to shut off). In the "on" state, there are six sub-states, including idle 607 (with the UV lights off), timing 609 (e.g., when the apparatus is running a cycle, and UV lights are on), and four externally controlled states (which are optional), which may separately control the one or more UV-LEDS. In FIG. 6 the examples show an external off control state 611 (with all of the UV LEDs off), a first external on sub-state 613 (with the first UV LED on, but the second UV LED off), a second external on sub-state 615 (with the second UV LED on, but the first UV LED off), and an external all-on control 617, with all of the LEDs on. Multiple additional sub-states may be included, such as additional timing states (e.g., additional cycles that may be run, such as quick sanitizing or longer sterilization cycles, etc.). The functions of the state diagram shown above may be performed by the controller (control circuitry. For example, the control circuitry may control operation of the indicator and UV LED's, the controller may control timing functions, UV on time, UV LED Duty cycle, idle time, etc. The controller may detect and/or process inputs (e.g., may scan for inputs from the one or more controls, including hosting control signals with debouncing, lid status, CapSense key, etc.). The controller may update outputs from the device, including display outputs (e.g., the indicator LED(s) on the outside cover), and/or may control communications with one or more outside controllers (e.g., external hosts). The controller may also update the outputs, including monitoring and/or updating the lid status (open/closed) and may transmit this to the external host and/or use it internally. Finally, the controller may provide basic power management functions, such as turning on/off clocks and function blocks as needed.

Figure 7A:
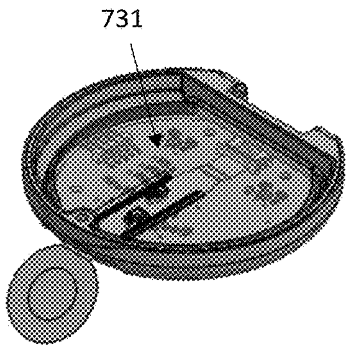
FIGS. 7A-7C illustrates another example of an apparatus for sanitizing and/or sterilizing a dental/orthodontic appliance, showing the control circuitry without a bottom covering surface (FIG. 7A), partially covered (FIG. 7B) and covered (FIG. 7C).
Figure 7B:
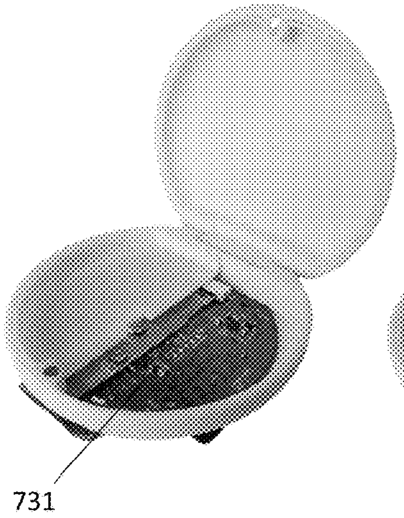
Figure 7C:
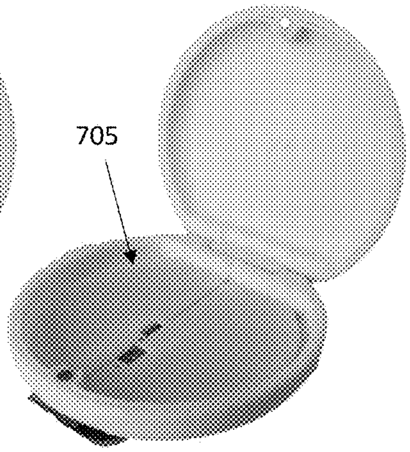

FIGS. 7A-7B show one examples of the control circuitry within the housing of an example apparatus, beneath the lower base 705 of the apparatus. FIG. 7A shows the control circuitry 731 exposed with the lower base removed. In FIG. 7B half of the lower base has been attached, while in FIG. 7C the lower base cover has been attached, forming the bottom of the chamber between the top and the lower base.

The control circuitry may provide timing control for the one or more cycles (e.g., disinfecting cycles, including cycle duration, such as short/sanitizing, long/sterilizing, etc.), control of the UV LED drivers, control of the user LED indications of the various states, control the monitoring of the lid state, such as lid open/closed and thus override protocols for disabling/enabling UV LED power. In some examples the controller may also or alternatively receive external control signals, as mentioned above.

In some examples, the case closer detection may be detected by one or more magnetic sensor that may detect when the case is closed or opened by sensing a magnet when the case is closed. For example, a magnetic sensor may signal the controller (e.g., control software) to control the UV LED's drivers. In some examples an LED indicator may be place "on" (such as a green LED) when case is closed. The controller may also control a UV Active Indication that may be illuminated when the UV-LED(s) are on, emitting UV light within the apparatus. For example, an amber-colored LED, may indicate when the UV LEDs are active either by user control or via external control.

As mentioned above, any of these apparatuses may process and act on inputs from one or more controls on the apparatus (e.g., on the outer surface of the apparatus). A user may press a power button to start the disinfecting cycle, the amber LED blinks 3 times before activating the UV LED's. The control may detect the pressing, as well as the duration of the pressing. In this example, when the control detect that the control is continuously pressed, the UV LED's may be activated (turning the cycle "on". In some examples, the controller and one or more controls (e.g., buttons) on the apparatus may be activated by the user to initially begin a 30 second disinfection cycle. For example, the user may activate the control by touching a capacitive power button on the apparatus. In some examples, the user may cancel a cycle (e.g., a disinfection cycle) by detecting activation of the control input (e.g., button) or a separate control input (e.g., button, slider, etc.) on the device; for example, the user can cancel a disinfection cycle by pressing the power button again.

As mentioned, in general these apparatuses described herein may include a power source; the power source may be a battery providing battery power (e.g., in some examples one or two AA or AAA batteries may be used).

As mentioned above, also described herein are apparatuses that are configured for tabletop, rather than compact (e.g. portable) use. For example, described herein are cleaning devices that are configured for point-of-care (e.g. bedside, within a patient's bathroom, etc.) operation. These apparatuses may be larger than the portable devices described above but may incorporate any of their other features. For example, these apparatuses may include two or more treatment modalities (e.g., UV, ultrasound, heat, etc.). In some examples, the apparatuses include ultrasonic cleaning alone or in combination with other treatment modalities, such UV treatment. For example, the disinfecting device can utilize both UV and ultrasonic cleaning. The UV may be applied concurrently or separately than the ultrasound. As shown in FIG. 8, an ultrasonic and/or heating tank may be included in addition to one or more UV LEDs to provide light. The liquid can include a cleaning material (e.g., detergent, disinfectant, etc.), which may be added to the liquid tank for the ultrasonic cleaning process.

Figure 8A:
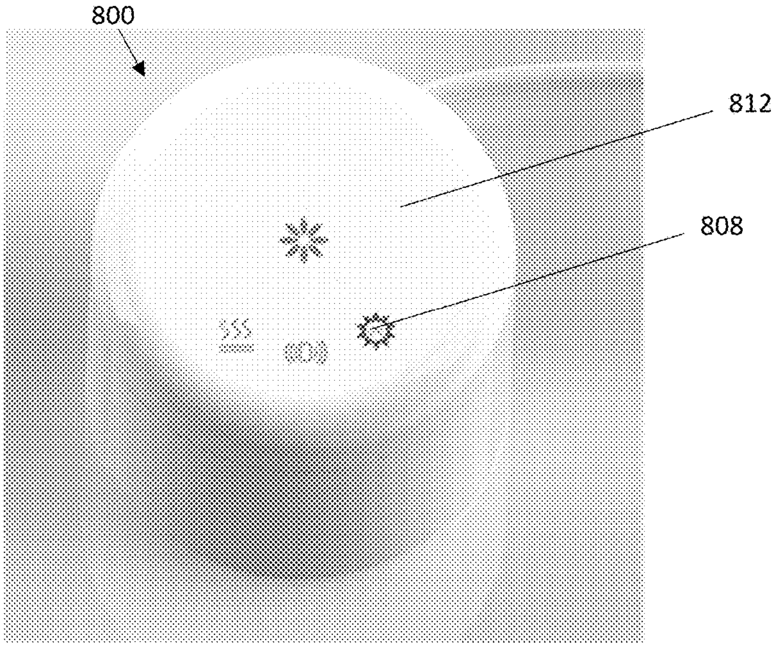
FIGS. 8A-8C illustrate an example of an apparatus for sanitizing and/or sterilizing a dental/orthodontic appliance, configured as an ultrasonic cleaning apparatus (with or without UVC LEDs).
Figure 8B:
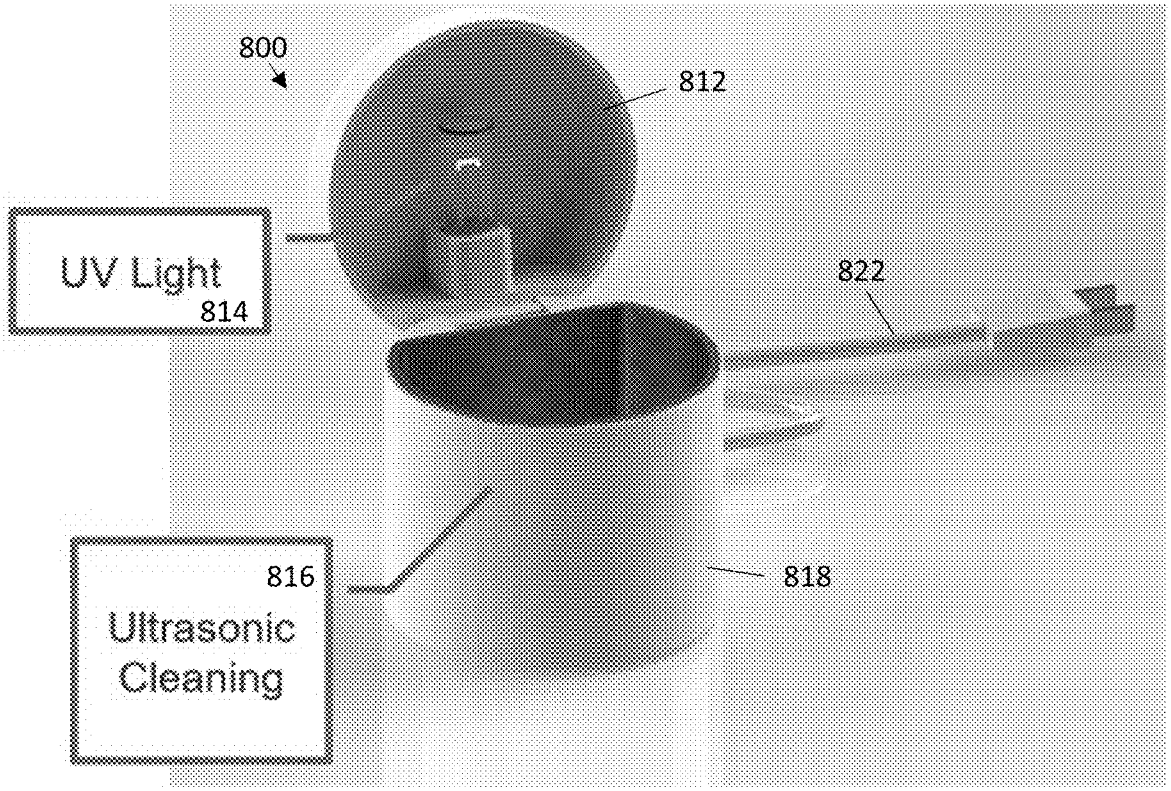

In FIGS. 8A-8B, one or more controls (e.g., capacitive touch buttons) 808 may be included on the apparatus 800, such as on the top surface of lid 812, so that user can select the cleaning mode (type, duration, quick/sanitization, longer/sterilization, etc.) and/or duration. In FIG. 8B the apparatus is shown with the lid opened, showing the UV light source on the lid (one or more light sources, such as UVC-LEDs may be used). The base 818 portion includes a tank chamber and a tray region for holding one or more dental appliances. The base may include the control circuitry and one or more ultrasound transducers for ultrasonic cleaning 816. The tray region and/or top and/or sides may be UV reflective, as described above. In some examples the base is configured to heat the fluid (e.g., water, cleaning solution, etc.) for cleaning. For example, the apparatus may be configured to heat the fluid to 60 degrees C. (e.g., up to about 50 degrees C., up to about 55 degrees C., up to about 60 degrees C., up to about 65 degrees C., up to about 70 degrees C., up to about 75 degrees C., etc.). The apparatus may include a temperature sensor to prevent it from overheating the water or going beyond a pre-set temperature, which may prevent damage to the dental appliances (e.g., aligner, retainer, etc.).

The apparatus may include a dedicated (e.g., wall) power connection (cord 822). Alternatively, the apparatus may be powered by a USB cable and/or an internal battery (in some examples, a rechargeable battery).

Figure 9A:
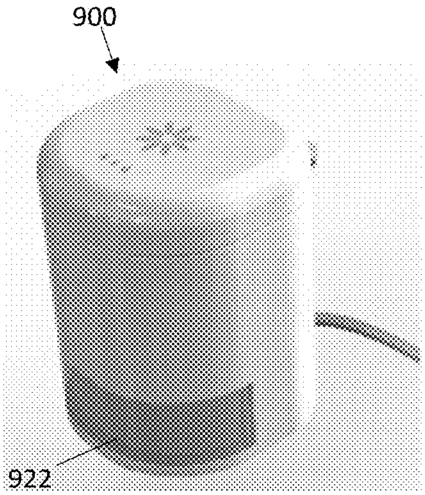
FIGS. 9A-9C illustrate another example of an apparatus for sanitizing and/or sterilizing a dental/orthodontic appliance, configured to apply ultrasonic energy as part of the cleaning process, including a vortex drain.
Figure 9B:
Figure 9C:
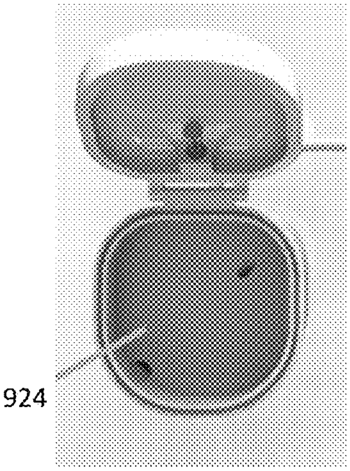

In some examples, these apparatuses may include forced circulation. FIGS. 9A-9C illustrates an example of a tabletop apparatus 900 for disinfecting a dental appliance that is similar to that shown in FIGS. 8A-8B. The apparatus includes a tank 922 and an internal chamber 924 that is fluidly connected to a fluid reservoir from which it may be filled. The chamber, as shown in FIG. 9C may include one or more fluid flow paths. In FIG. 9C, the flow path is configured for vortex drainage. The apparatus includes a cleaning circulation system. This circulation system can generate water flow from a bottom cartridge or tank 922 (that may include a cleaning chemical) up to the chamber configured to hold the appliance (e.g., aligner). Contaminants may be washed off from appliance and be drained back a waste reservoir in the bottom of the device. The waste reservoir may be emptied after one or more uses, and the tank may be refilled. In some examples the base may include a removable/replaceable cartridge that holds the fluid and/or waste reservoir. A cartridge may include one or more fluid connections to the base. The apparatus may also include one or more pumps and/or valves. In some examples the apparatus may be configured to allow gravity to drive fluid from the tank (which may be positioned above the chamber holding the appliance, including in the lid) and into the chamber, while the waste receptacle is below the chamber. The apparatus may include valves for controlling flow of the fluid between the tank and the waste.

In FIGS. 9A-9C the apparatus includes a UV light source for cleaning, as well as a fluid tank, and is configured for forced circulation of fluid within the chamber. In some examples, the chamber also includes a sloped lower surface for post-cleaning drainage into the waste chamber.

Figure 10A:
FIGS. 10A-10C show another example of an apparatus for sanitizing and/or sterilizing a dental/orthodontic appliance, as described herein.
Figure 10B:
Figure 10C:

FIGS. 10A-10C illustrate another example of a countertop apparatus that is configured for ultrasonic cleaning. In this example one or more UVC LED to provide UV sanitization/sterilization can be combined with one or more ultrasonic transducer for effective cleaning of dental appliances. In addition, one or more visible-light LEDs can be incorporated into the outside of the apparatus as an output, providing a visual indicator for the status of the device such as On/Off, by changing the LED color. Also the visual indicator can be used as a timer to indicate the progress of the operation of the apparatus, e.g., by illuminating a series of LEDs to indicate the progress.

Any of the apparatuses described herein may also be configured to assist in other dental hygiene. For example, any of these apparatuses may be configured to provide guidance for a user's daily routine related to dental hygiene such as brushing teeth. For example, a user can use the apparatus to disinfect a dental appliance (e.g., aligners/retainers) while brushing their teeth; the apparatus may have a preset timer for optimal teeth cleaning time (such as, e.g., about 2 minutes). The apparatus can alert the user that sufficient teeth cleaning time has passed at the end of the disinfection. These apparatuses can include one or more outputs, such as a display, LEDs, speakers, etc. to alert the users of its current status.

In some examples, a portable disinfection apparatus (e.g., case) may be used as a battery storage or backup (e.g. power bank) to charge other electronic devices. Thus, the apparatus (e.g., a case) may include one or more additional ports for coupling to an electronic device or it may use the same port as for charging (e.g., a USB port).

The apparatuses described herein may be configured to connect to wirelessly connect to a processor (e.g., a smartphone, a pad, table, laptop, etc.). The apparatus, and in particular the controller, may be configured to wireless transmit and receive information to a remote processor such as a smartphone. The remote processor may be running application software allowing the remote processor to communicate with the apparatus, including sending/transmitting data. For example, the apparatus may transmit use data to the remote processor (e.g. phone), and/or receive command instructions from the remote processor (e.g., turn off, turn on, etc.). Thus, the remote processor may track certain activities (e.g. how long/often a dental appliance has been cleaned, teeth brushing/cleaning time, aligner/retainer wear time, etc.).

In some examples, the disinfection apparatus (e.g., case) can have a sensor to detect the presence of the appliance (e.g., an aligner, retainer, palatal expander, etc.) to monitor how often/long orthodontic appliances stay inside the device. In some examples the disinfection UV LED can be used as a light emitter or transmitter for a detection sensor. A biosensor can be integrated into the disinfection device to monitor the presence of microorganisms (e.g. bacteria, virus, fungi, etc.). The disinfection device can actively monitor the progress while disinfecting and may be configured to automatically turn off when no more bacteria or virus is present (or when the detect biomarkers for one or more pathogen falls beneath a threshold).

The methods and apparatuses for sanitizing and/or sterilizing described herein may be configured to improve the efficacy of the use of UV (including UVC). In particular, the portable apparatuses described herein may be configured to enhance the effect of UVC to disinfect a dental/orthodontic appliance (such as, but not limited to an aligner, retainer, palatal expander, etc.).

Most of bacteria, protozoa, virus, and yeast can be killed under 10 mJ/cm$^2$ UVC dose exposure for 1 log reduction (90% kill) and 20 mJ/cm$^2$ for 2 log reduction (99% kill). By using UVC LED, 0.1 mW/cm$^2$ intensity may be a threshold for 3-5 min disinfection duration. In general, the dental/orthodontic appliances for use with these apparatuses may be formed of a material that may absorb and/or attenuate the applied UVC light, which may increase the challenge of disinfecting these apparatuses. For example, an appliance may include one or more layers of material (e.g., ST30 or EX40) that will reduce initial UVC intensity to 10% of its original value. In addition, the intensity of the UVC LED light intensity falls proportional to one over the square of the distance (1/d$^2$), and the angle of the light may also modify the intensity (e.g., the intensity may be halved when the angle is approximately 120 degrees). Although, as mentioned above, the chamber of the apparatuses (e.g., cases) described herein may be coated with a UV-reflective coating, such as aluminum, which may reflect at least 50% of the light within the chamber, additional modifications may further enhance the energy applied to the appliance(s) held with the chamber of the apparatus.

Figure 11A:
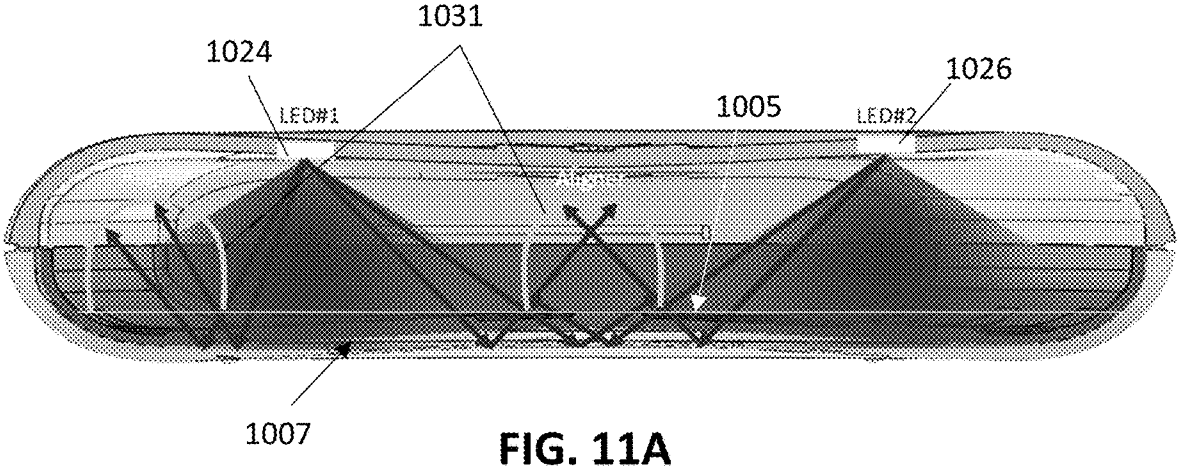
FIG. 11A is a section through another example of an apparatus for sanitizing and/or sterilizing a dental/orthodontic appliance similar to that shown in FIGS. 2 and 3A-3C, including a frame or stand for holding the one or more appliances above the bottom (UV-reflective bottom) of the chamber of the apparatus.
Figure 11B:
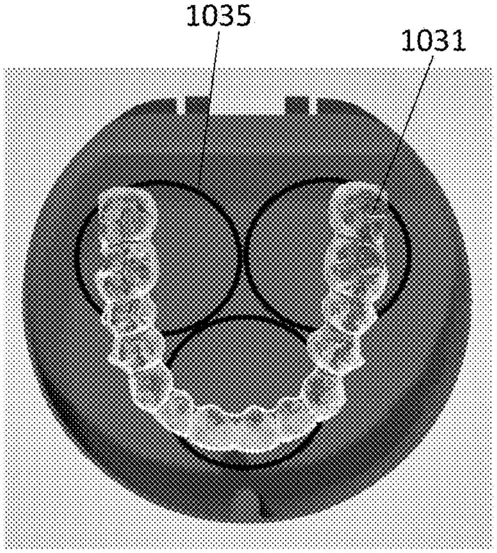
FIGS. 11B-11C illustrate examples of frames for apparatuses as described.
Figure 11C:
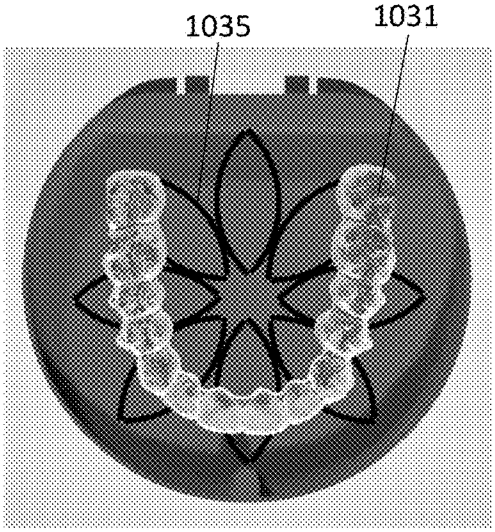

In some examples, the apparatuses described herein may be configured so that the appliance is lifted up from the base of the chamber allowing the reflective underside bottom surface of the chamber to direct more light to the underside of the appliance. For example, FIGS. 11A-11C illustrate examples in which a thin support is arranged on the bottom of the chamber to allow light to reflect up from beneath the appliance when the appliance is resting on the support at the bottom of the chamber and when UV light (e.g., UVC) is emitted. In FIG. 11A, the UVC is being emitted from the top of the chamber (e.g., a lid).

In cases where an appliance material has a high absorption for UVC light, the inner surface that is not directly exposed to UVC light typically may not receive enough UCC light (enough intensity) to kill pathogens such as bacterial or virus as compared to regions that are directly exposed. In some examples the inner surface of the case may include a highly reflective material 1007 (e.g., and Aluminum coating) and the appliance (e.g., aligner, retainer, palatal expander, etc.) may be lifted up from bottom using support or frame 1005, as shown in FIG. 2. In this way, UVC light emitted by LEDs #1 1024 and #2 1026 can be reflected back into the inner surface of the appliance 1031 (shown in cross-section in FIG. 11A). Aluminum has a relatively high reflectance in UVC wavelength range. The frame or support may be a solid material (e.g., a sheet or layer) or a grid or mesh material or may form a pattern that may support the appliance(s) above the reflective bottom of the chamber. In some examples the frame or support may form a shape or pattern that has smaller gaps or openings than the diameter of the appliance to be held within the chamber. For example, FIGS. 11B and 11C illustrate examples of frame that may be positioned on the bottom of the chamber. In FIG. 11B the frame 1035 has a three-ring design on which the appliance (shown as an aligner 1031) rests. In FIG. 11C the frame 1031 has an eight-petal flower design on which the appliance 1035 rests. The frame may create a gap between appliance and the bottom of the case, as mentioned. In general, the support (e.g., frame) may have a height that is between about 2 mm and about 4 mm. In some examples the total height of the chamber (internal cavity or internal chamber) of the apparatus may be about 16 mm. The arms or walls (forming the shape/grid pattern) of the frame may have a width that is between about 1 mm or less, which may avoid interference of the UVC light.

In some cases, the frame is formed of a UV-transparent material (or a material that is substantially UVC transparent, such quartz) or a UVC-reflective material. As mentioned, the frame may be thin and sparse (e.g., having larger openings allowing passage of UVC reflected from the bottom surface), so that it does not block the reflected UVC.

In some examples, the frame may be a separate part that can be removed from the tray (e.g., the bottom of the chamber), and different shapes or geometries can be used depending on overall aligner size and height. Alternatively, the frame can be a permanent part of the middle tray (chamber bottom), so the frame shape can be molded into the tray during manufacturing. In some examples, the frame may be coated or formed of a UV reflective material, such as Aluminum.

Figure 12:
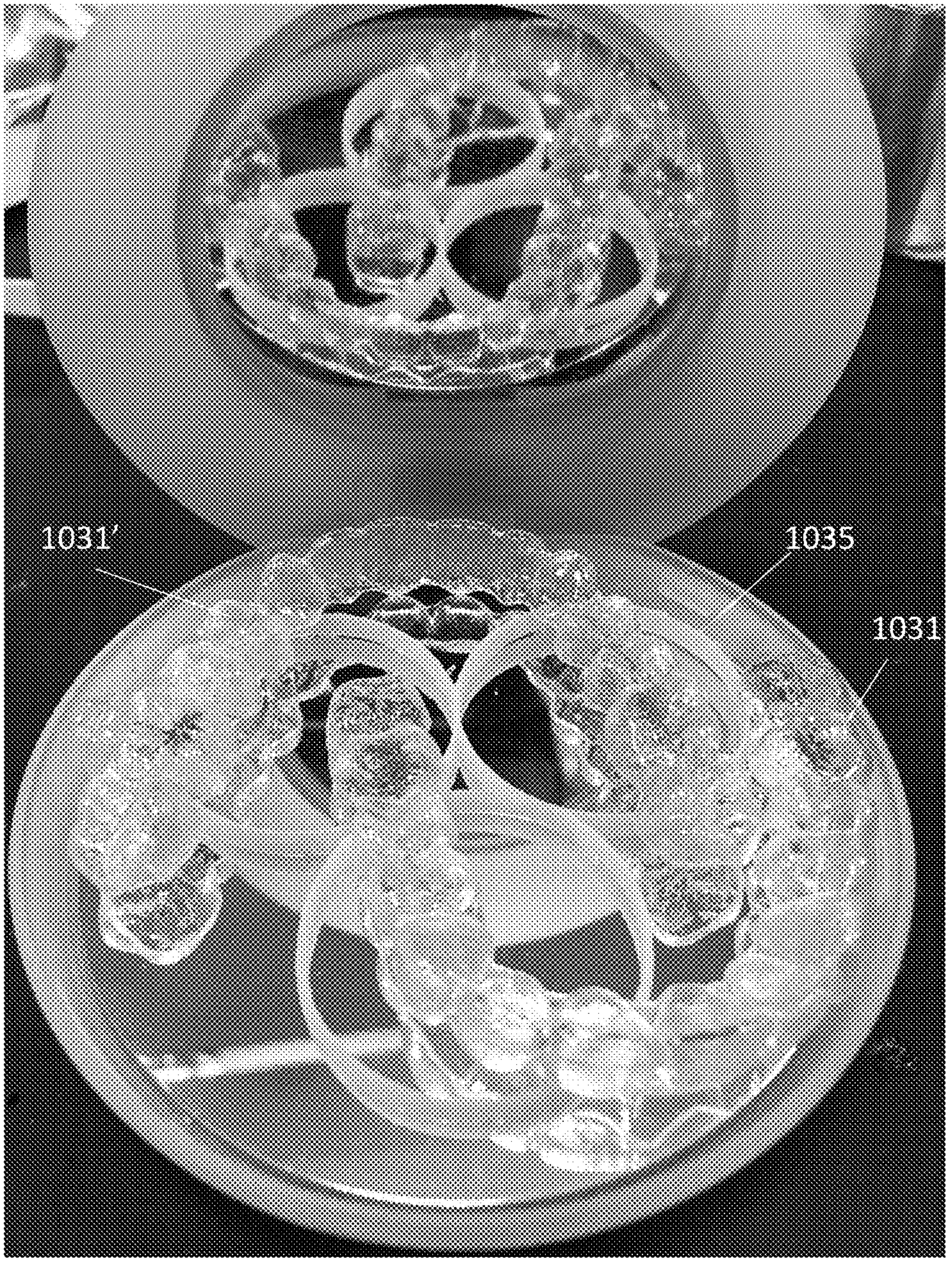
FIG. 12 is another example of an apparatus for sanitizing and/or sterilizing a dental/orthodontic appliance including a frame for holding the one or more dental appliances above the reflective bottom of the apparatus.

FIG. 12 shows another example of an apparatus, shown with the lid open, exposing a bottom tray region that include a reflective coating, onto which a support (frame) is included, and a pair of dental/orthodontic appliances (shown here as a pair of aligners 1031, 1031') are resting atop the support 1035. The top lid also includes a UVC reflective material (e.g., aluminum) and the UVC-LEDs may be on this top lid, within the chamber (or arranged so that their light is directed into the chamber. In any of these examples, the controller (including power supply) and/or LEDs may be closed to enable operation of the UVC-LEDs only when the lid is secured closed.

Any of the apparatuses described herein may be configured so that the appliance(s) held within the apparatus may move relative to the applied sanitizing/sterilizing material (e.g., UV light, ultrasound, heat, etc.). For example, in any of these apparatuses, the bottom of the chamber formed within the apparatus for holding the appliance(s) may rotate (or may include a frame that rotates) when the UV light is being applied. In some examples the base of the apparatus may include a motor with one or more gears for rotating all or portion of the bottom of the chamber (such as a support or frame) in order to rotate the apparatus with respect to the UV light(s). The bottom of the chamber may be referred to herein as the tray of the apparatus and in some examples may be a rotating tray. For example, FIGS. 13A and 13B illustrate apparatuses (shown in cross-section) for sanitizing and/or sterilizing a dental appliance held within the apparatus in which the bottom of the internal chamber is configured to rotate.

It may be advantageous to have a more uniform distribution of UVC light intensity inside the chamber of the apparatus (e.g., case). If the intensity is too low, bacteria or virus cannot be killed within a practical operation time (1-10 min). If the intensity is too high, UV radiation can degrade and discolor appliances (e.g. leading to yellowing). Appliances (such as aligners) may be positioned by the user in a somewhat random manner, and in some cases, different parts of the aligners may receive different UVC intensity, and some area may not receive sufficient UV dose to kill bacteria. In order to ensure sufficient and uniform coverage of the UV light inside the chamber in some examples the tray may be actuated to provide a rotational motion, as illustrated in FIGS. 13A-13B. In FIG. 13A the apparatus includes a rotational tray 1311 within the chamber 1308. The rotational tray may also be UCV reflective (e.g., may include an aluminum material or coating). The appliance 1331 may rest on the rotating tray 1311, and the tray may rotate it to change the relative position of the appliance to LEDs 1324, 1326 within the chamber. A passive or active motor may provide power to rotate the tray on which one or more aligners sit. Alternatively, rather than rotating, the tray actuation may be linear instead to move the aligners in a different direction or orientation. In some examples the tray can be actuated to move aligners in random positions and directions. This random motion can create uniform distribution of the UV dose to disinfect all the surfaces of the aligners.

Figure 13A:
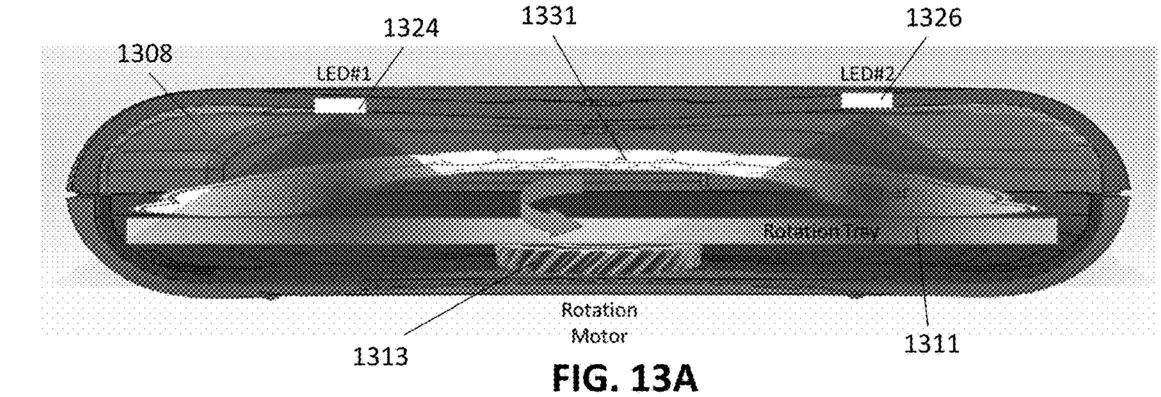
FIGS. 13A-13B show section through examples of apparatus for sanitizing and/or sterilizing a dental/orthodontic appliance in which the appliance to be sanitized and/or sterilized may be rotated relative to the UVC LEDs.
Figure 13B:
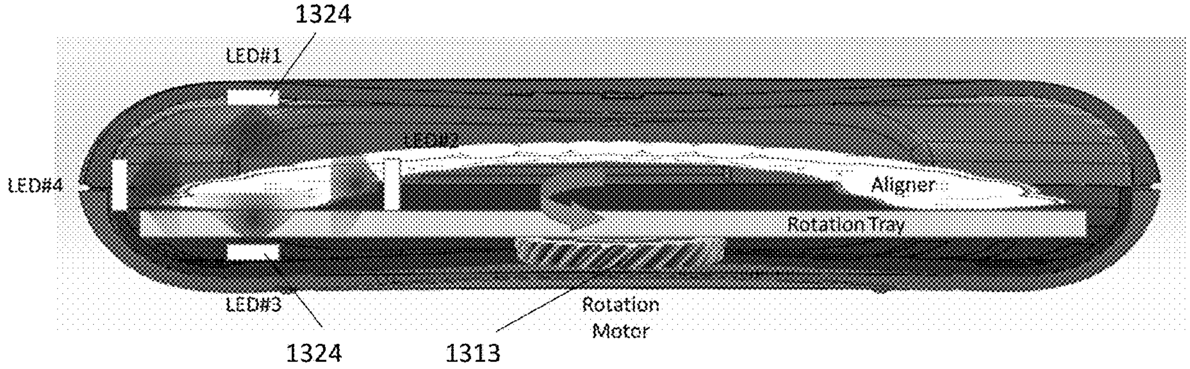

FIG. 13B illustrates another example in which the aligner 1331 is rotated within the chamber 1308 by a motor 1313, similar to that shown for FIG. 13A. However, in FIG. 13B a plurality of LEDs are directed (with greater intensity) within one region of the chamber into which the appliance is rotated through. In FIG. 13B four LEDS are shown in one region, illuminating from the top and bottom (and optionally, left and right).

Alternatively or additionally, in some examples the UVC LEDs may be actuated, e.g., by rotating relative to an appliance held within the apparatus. For example, the apparatus may be configured so that one or more of the UV (e.g., UVC) LEDs are mounted to an actuator which can move relative to the appliance when it is held within the chamber. For example, the one or more UVC LEDs can be mounted onto an actuator which can move or rotate around to position and orient the UV light to scan and cover multiple areas inside the chamber. Thus, all or most of the surfaces of an appliance can be exposed to the UV light and bacteria/virus can be effectively killed.

Figure 14:
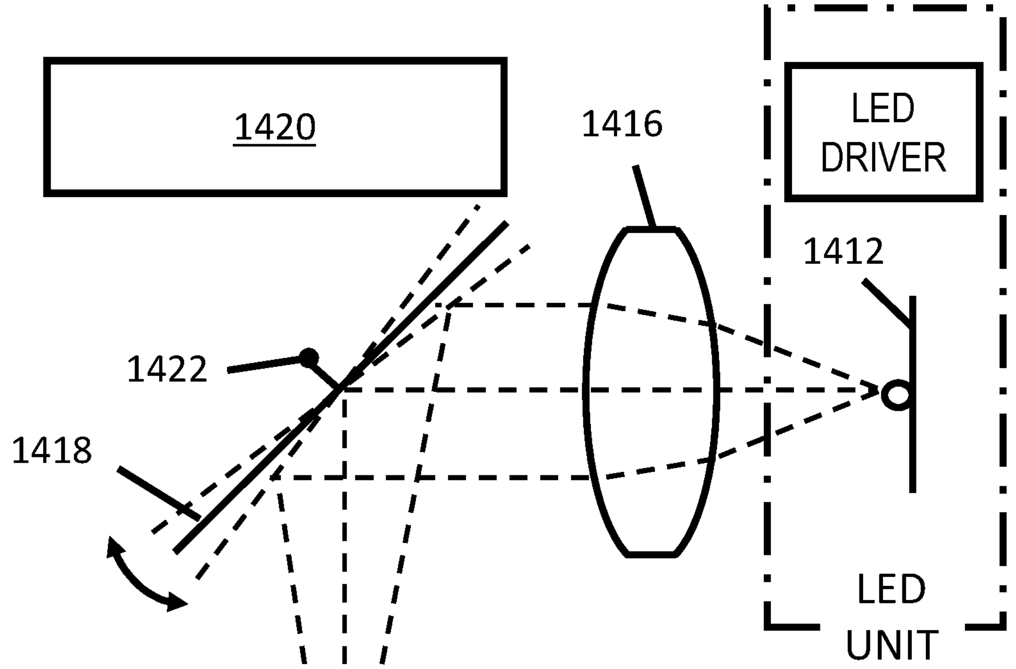
FIG. 14 illustrates an example of a scanning sub-system that may be used as part of an apparatus for sanitizing and/or sterilizing a dental/orthodontic appliance, as described herein, for scanning UVC light over an appliance within the apparatus.
Figure 15:
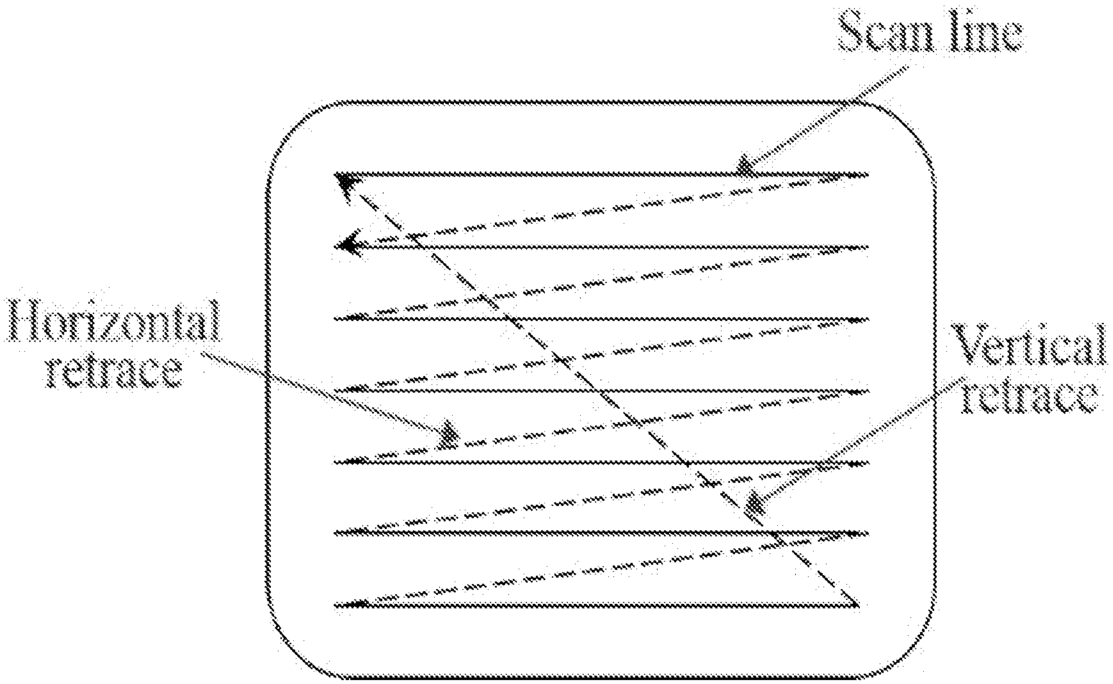
FIG. 15 shows an example of one scan pattern that may be used for UV sanitization and/or sterilization within an apparatus for sanitizing and/or sterilizing a dental/orthodontic appliance, as described herein.

In some examples, optics may be included to scan or otherwise move the UVC light relative to the appliance. For example, one or more scanning mirrors may be included to direct light relative to an appliance. As shown in FIG. 14, a few (e.g., in some examples just one) UV light source having a relatively a thin and wide beam pattern may be used with a mirror to scan a pattern across a chamber of an apparatus (housing one or more appliances) so that the entire appliance may be sanitized and/or sterilized. This configuration may reduce the cost of the apparatus by using a single light source and optic to cover the entirety of the case with a high dosage of UV. In FIG. 14 the apparatus includes an LED unit (LED driver, LED) and a lens 1416 that focuses the light onto the mirror 1418 so that it can be moved by a drive circuit 1420 coupled to an actuator 1422. A sensor may be included to help steer the mirror. Any appropriate scanning pattern may be used, including a raster pattern, as shown in FIG. 15. In some examples a single concentrated UV light source and two mirrors may be used to scan across the entirety of the case in length and widthwise path or similar path to cover the area the aligner sits. This would allow for an even higher dosage of UV and allow sterilization to be completed more quickly.

Figure 16:
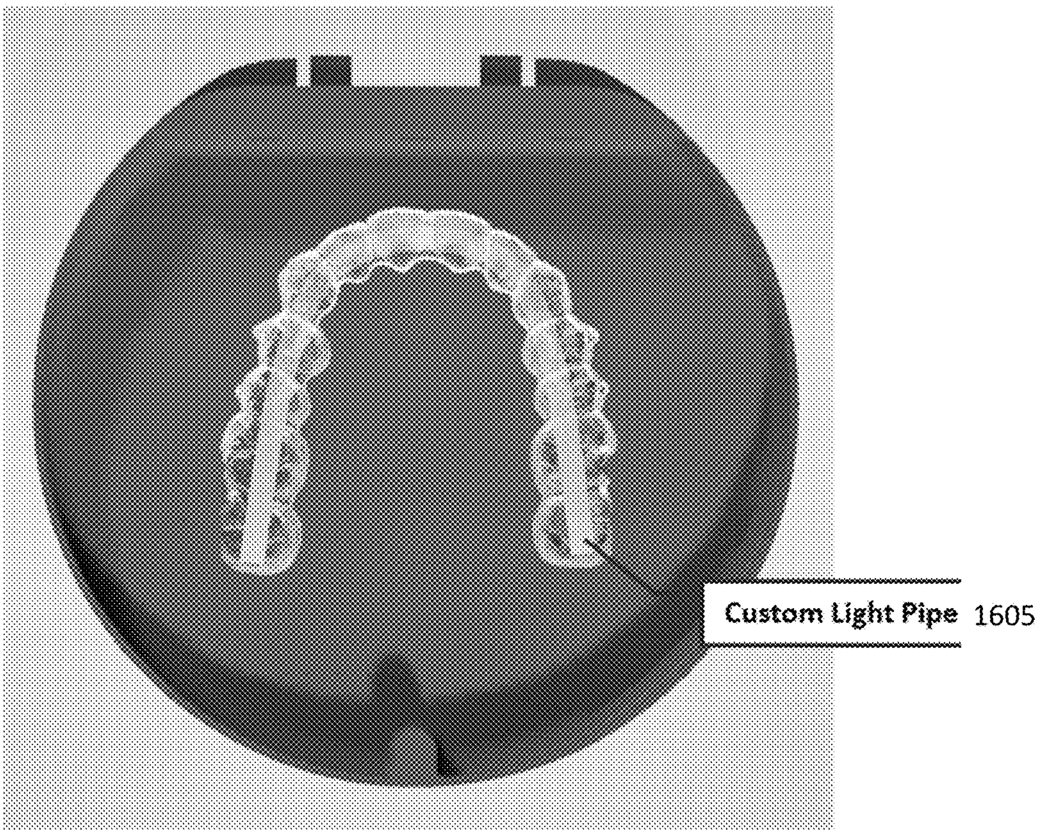
FIG. 16 shows another example of an apparatus for sanitizing and/or sterilizing a dental/orthodontic appliance, including a light pipe for delivery of UV light to the appliance within the apparatus.

Alternatively or additionally, in some examples the apparatus may include a custom light pipe that may direct the light within and/or around an appliance. For example, a light pipe in the shape of a dental arch can be include, and one or more UVC LEDs may apply UV light (e.g., from one or both ends) into the light pipe. The piping material can be tuned such that total internal reflection occurs throughout the majority of the pipe at a given UV wavelength, with etched openings or protrusions that allow for a sharper light angle to escape at given points along the pipe length. A light pipe may be combined with a scaffold or fixture for the location of a given dental/orthodontic appliance, which may allow for maximum selective wattage delivery to surface areas of interest. For example, FIG. 16 illustrates one example of an apparatus including a custom light pipe 1605.

Figure 17:
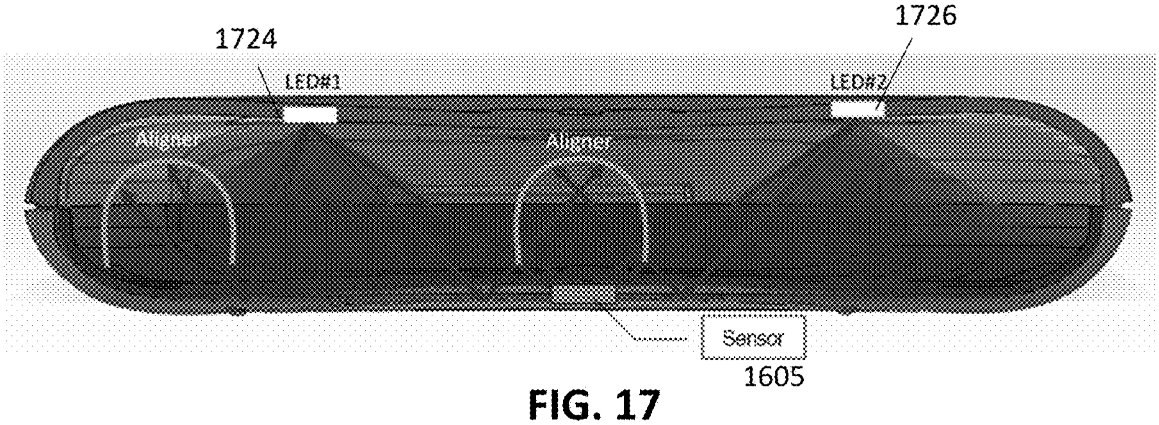
FIG. 17 is a section through another example of an apparatus for sanitizing and/or sterilizing a dental/orthodontic appliance, including a UV sensor for detecting the intensity of the UV light within the apparatus.

Any of the apparatuses described herein may include one or more sensors to detect (and in some examples, apply feedback on) the intensity of the applied UV light. Typically, UV light sources have a limited lifetime (e.g. 1,000-20,000 hours). One or more sensors may help ensure sufficient and reliable UV dose each time the UV light source is turned on. For example, a sensor can be integrated as a part of a UV disinfection apparatus; the sensor may provide input into the controller. For instance, the sensor can measure the UV light intensity and/or dose level and may indicate if the UV light source is near the end of lifetime. Also the sensor can measure the UV light intensity in real time and control the electrical voltage or current powering the UV light source such that each time a consistent level of UV dose is generated for sufficient germicidal efficacy. FIG. 17 illustrates a section through one example of an apparatus including a UV sensor 1708 and one or more UV LEDs 1724, 1726. The sensor may provide real time monitoring and feedback control of the UV light intensity.

EXAMPLES

Figure 8C:
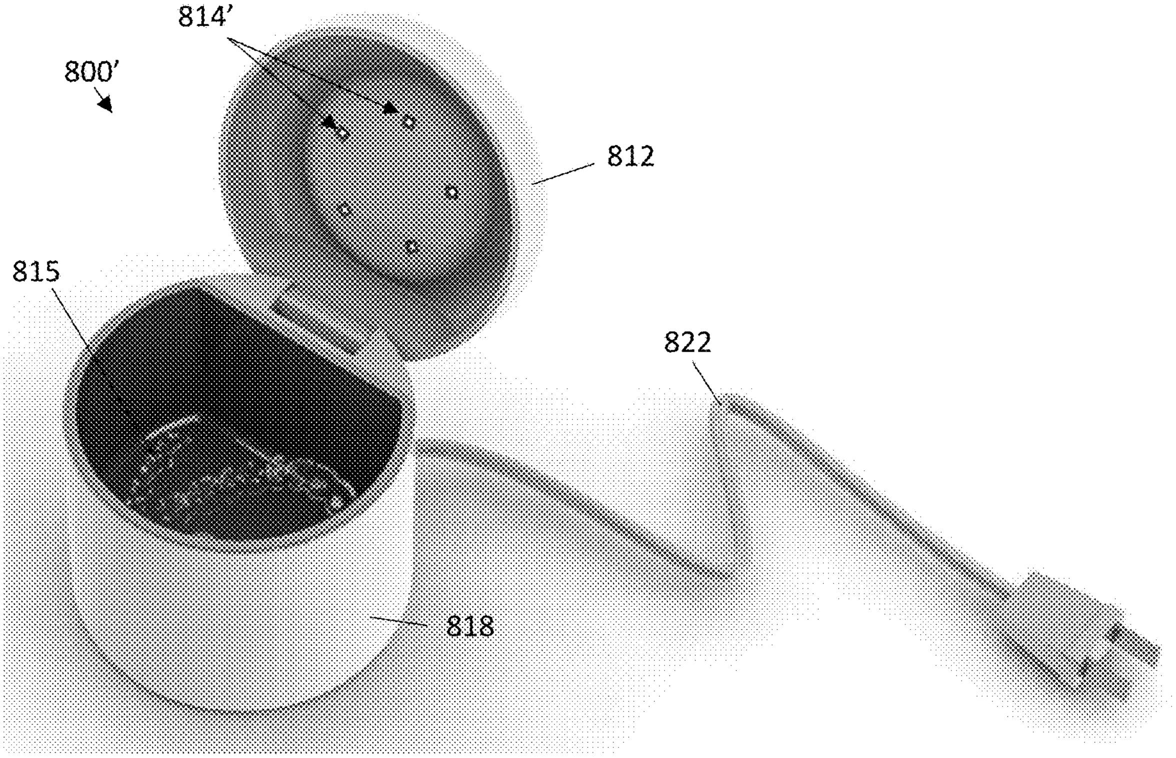

As mentioned above, in general, the methods and apparatuses may include more than one energy modality applied to clean a dental appliance. Thus, in some examples the apparatus or method may include one or more sources of light (e.g., UV light, as from LEDs such as UVC-LEDs, lasers, etc., or in some cases visible light) for applying light energy in addition to ultrasonic energy for mechanically cleaning (e.g., by cavitation). FIG. 8C shows another example of a cleaning apparatus configured to apply both light (e.g., visible light) and mechanical (e.g., ultrasound) energy to clean a dental appliance. In FIG. 8C, the apparatus includes one or more controls (e.g., capacitive touch buttons) on the apparatus 800'. As shown in FIG. 8A, the controls may be on the top surface of lid 812, the side, etc. (or may be separate from the device, and wireless couple to the device), so that user can select the cleaning mode (type, duration, quick/sanitization, longer/sterilization, etc.) and/or duration, or a pre-set operational mode.

In FIG. 8C the apparatus is shown with the lid 812 opened, showing a plurality of visible light sources 814' (five are shown) integrated into the lid. One or more visible light sources, such as LEDs may be used. The base 818 portion includes a tank chamber for holding one or more dental appliances 815. The base may include the control circuitry and one or more ultrasound transducers for ultrasonic cleaning. The tray region and/or top and/or sides may be optically reflective, as described above. In some examples the base is configured to optionally heat the fluid (e.g., water, cleaning solution, etc.) during cleaning. For example, the apparatus may be configured to heat the fluid to 60 degrees C. (e.g., up to about 50 degrees C., up to about 55 degrees C., up to about 60 degrees C., up to about 65 degrees C., up to about 70 degrees C., up to about 75 degrees C., etc.). The apparatus may include a temperature sensor to prevent it from overheating the water or going beyond a pre-set temperature, which may prevent damage to the dental appliances (e.g., aligner, retainer, etc.).

The apparatus may include a dedicated (e.g., wall) power connection (cord 822) and/or a battery. For example, the apparatus may be powered by a USB cable and/or an internal battery (in some examples, a rechargeable battery). In the example shown in FIGS. 8A-8C, the apparatus may be configured to clean a dental appliance (or multiple dental appliances) through both ultrasonic action (e.g., cavitation) and visible light irradiation. In general, the cleaning and/or disinfection of removable dental devices may use mechanical action, such as ultrasonic cavitation, and may deactivate pathogens through irradiation using visible light, in some examples, using blue light in the spectrum of 400-470 nm. The use of visible light spectrum to inactivate pathogens in combination with ultrasonic action to mechanically remove them from dental appliance may be particularly effective and may prevent damage to the dental appliance. In addition, visible LED wavelengths (between 400-470 nm) are eye safe and may also provide a visible indication of the operation of the apparatus.

The use of both visible light and cavitation by ultrasound is surprisingly effective at cleaning the aligners. Preliminary testing using a variety of pathogens including bacteria typically found in the oral environment showed significant inactivation and removal of both bacterial contamination and byproducts.

In examples using visible light, the apparatus does need a safety switch (or lock) to shut off a UV light source; variations including UV light may benefit from such a safety switch or interlock, as UV light can cause damage (e.g., burns) to the cornea, and thus UV emitters must be shut off when cover of device is opened. In addition, there may be less damage and/or yellowing to polymer materials such as those used in dental appliances (e.g., dental aligners and dental devices).

Any appropriate visible light source may be used, including well-known high-output 400-470 nm LEDs. As shown in FIG. 8C, the use of a metal tank that is resilient to ultrasonic cavitation may also be used. In this example, ultrasonic energy is produced in a cleaning fluid or agent, such as a composition of water, a surfactant and/or a sterilizing agent, or any combination of these. Thus, a dental appliance 815 placed in the tank 818 of the apparatus 800' can be cleaned through the mechanical cavitation action to release pathogens and biofilm formed on the surface of the appliance. One or more visible light sources, e.g., emitting within the range of about 400-470 nm wavelength can be shone onto the surfaces of the dental appliance and through the cleaning agent within the tank to inactivate pathogens released into the liquid and on surfaces of the dental appliance.

Although the cleaning device shown in FIG. 8C is semi-portable (e.g., being plugged into a wall power source, other variations may be smaller, more compact and/or may be fully portable (including a battery and/or USB power source). In some examples the cleaning apparatus may be pocket-sized (e.g., as a cleaning case that may be fully portable with battery and/or plug). These cleaning apparatuses may be waterproof.

Detection

As mentioned above, in general, the methods and apparatuses described herein may also be configured to detect and/or monitor the presence of microorganisms (e.g. bacteria, virus, fungi, etc.) including the byproducts of microorganisms, such as plaque. In some examples these apparatuses can actively determine if disinfection is necessary or helpful, and may monitor the progress while disinfecting and/or may be configured to automatically turn off when no more bacteria or virus is present (or when the detect biomarkers for one or more pathogen falls beneath a threshold). Further, these apparatuses can help monitor and provide feedback on the state of the patient's teeth, either by monitoring the dental appliance and/or by including one or more sensors on the dental appliance to monitor the teeth. The state of the dental appliance may surprisingly allow inference of the user's dental health, including indicating plaque, tartar, etc.

Thus, the apparatuses described herein may be used for intra-oral and extra-oral detection of biofilm, plaque and/or dental caries. For example, dental plaque causes many oral diseases (e.g. caries, gingivitis, periodontitis, and tooth decay). Plaque build-up can be a common problem during orthodontic treatments. The apparatuses described herein may be used to detect and monitor plaque, which may greatly assist users (e.g., patients) in maintaining their dental health, particularly when using an oral appliance such as, but not limited to, a dental aligner. Currently, there is no easy way for orthodontic patients to determine their oral health condition besides a dental exam. Non-patients or the general populations may have fewer dental visits to have their dental health checked. Oral hygiene and plaque build-up can become a significant health concern as people age.

The apparatuses and methods described herein may be useful for detecting and monitoring to provide consumer-level, real-time feedback for individual's oral hygiene and plaque detection; these methods and apparatuses may use the dental appliance (e.g., aligner) as a platform.

For example, plaque may be detected from the user's (patient's) teeth by one or more plaque detection mechanisms. For example plaque may be inferred or detected by optical sensing, e.g., using quantitative light-induced fluorescence. Plaque may be inferred or detected by intra-oral continuous pH measurement. Alternatively or additionally, plaque may be inferred or detected by use of a plaque disclosing dye with or without any of the apparatuses described herein.

For example, a non-invasive and consumer operatable method for detection of oral hygiene and aligner hygiene may include a direct visual feedback and measure of aligner cleanness and the effectiveness of any of the cleaning apparatuses described herein, such as (but not limited to) an ultrasonic cleaning apparatus. Thus, described herein are apparatuses that may act as a platform for a user or dental professional (e.g., orthodontist, general dentist, and researcher) to monitor a user's (e.g. a patient's) oral hygiene, such as identify and monitor bacteria, biofilm, and caries.

Currently plaque detection relies mostly on dental visits with professional examination and tools. Though recommended twice a year, many people may have fewer visits than ideal. Without effective and in-time removal of dental plaque, plaque build-up may cause many oral disease (caries, gingivitis, periodontitis, and tooth decay). For at-home diagnosis, although plaque disclosing tablets are commercially available, it is not widely adopted due to extra efforts required and user behavior change.

The methods and apparatuses described herein may provide non-invasive, real-time plaque detection, continuous monitoring, and do not require user behavior change.

Figure 18:
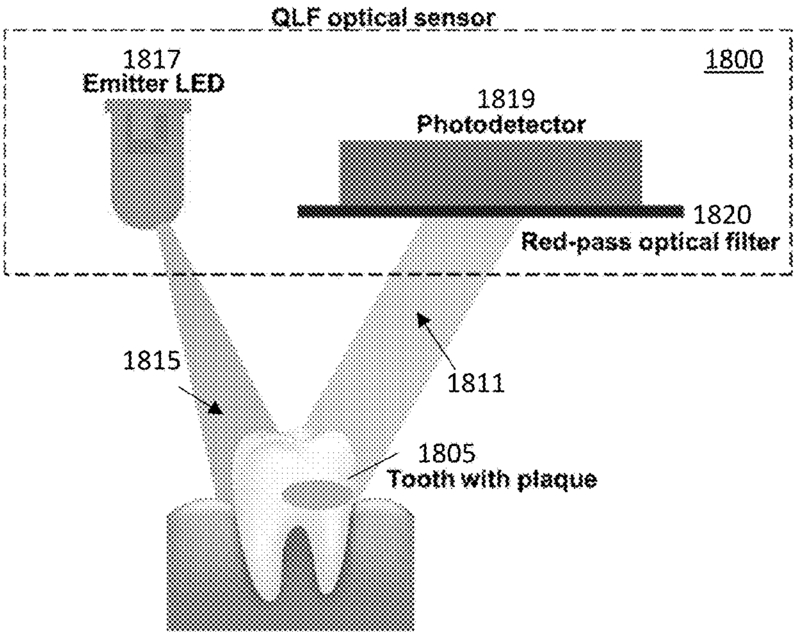
FIG. 18 schematically illustrates an example of a Quantitative Light-induced Fluorescence (QLF) sensing module that may be included with any of the apparatuses described herein.

For example, FIG. 18 illustrates one example of a method of plaque detection using optical sensing. It this example, the optical sensing includes quantitative light-induced fluorescence. Quantitative Light-induced Fluorescence (QLF) uses the fluorescence property of demineralized dentin and the visual contrast between sound tooth structure as compared with bacteria group (caries, protoporphyrin bacteria group, etc.) to detect plaque. Plaque may be detected by red florescence 1811 when blue-violet light 1815 is applied, as shown in FIG. 18. The sensing module requires an excitation light source 1817 (e.g., blue-violet light or in the UVA range of about 405 nm). The emission/response from a sound tooth structure is in light blue/green (emission wavelength in the range of about 430 nm-560 nm), while the emission/response from the bacteria group (e.g., mature plaque, dental caries, protoporphyrin, subgingival calculus) is in the red/orange region (emission of about 590 nm-700 nm). As shown in FIG. 18, a sensing module (e.g., a QLP optical sensor 1800) may include an optical emitter 1817 (e.g., an emitter LED, laser, etc.), an optical receiver 1819 (e.g., a photodiode, CMOS sensor etc.) and an optical filter 1820 (e.g., red-pass optical filter), which allows emission red florescence to be captured and filters out blue-violet excitation and emission lights.

In this example, the optical sensor is shown operating on a tooth. Alternatively a sensor may be included a part of a cleaning (or dedicated sensing) apparatus into which an aligner is positioned, in place of the tooth 1805 shown in FIG. 18. In this example, the QLF optical sensor may be used to detect light emitted by the bacteria or a bacterial byproduct (e.g., bacteria group) present on the aligner. The dental appliance (e.g., aligner) may be examined by a QLF detector to identify the presence of the bacterial marker as described above. The intensity of the signal may be correlated with the amount of bacterial and/or plaque. The dental appliance itself may pass the light or may emit outside of the red/orange region (emission of about 590 nm-700 nm).

Another example of method and apparatus for detecting plaque includes pH measurement. Tooth decay is known to be strongly associated with localized acidic pH. Acid saliva is around pH 5.0-5.8, moderately acidic saliva is usually pH 6.0-6.6, and healthy saliva is pH 6.8-7.8. The development of plaque and dental caries (e.g., tooth decay) significantly increases at low pH and oxygen-deprived environments. Saliva pH (measured on the floor of the mouth) between caries-free and extreme caries group may vary on average from 7.0 to 6.4. Any of the apparatuses and methods described herein may be configured to detect pH using a pH sensing module including a pH electrode and a reference electrode. Sensing may be performed using a sensor integrated onto the dental appliance (intra-oral sensing) and/or it may be performed after removing the appliance from the mouth, e.g., in a case or other holder including a sensor, such as (but not limited to) a cleaning apparatus as described above. For example, a dental appliance (e.g., aligner) removed from the patient's mouth may be inserted into a holder that includes pH sensing for the saliva on the appliance, particularly on the base of the appliance in closest proximity to the gingival region when the appliance is worn. For example, a holder may include one or more pH sensors (including electrodes, colorimetric sensors, etc.) for detecting pH from saliva on the appliance when inserted into the holder. If a colorimetric indicator is used, the color change may be detected optically (e.g., using an optical sensor) and a readout taken. Multiple readings may be made from different regions of the appliance. These different readings may be used to form an aggregate pH score that may be used as an indicator of dental health (e.g., plaque likelihood).

Alternatively or additionally, any of these methods an apparatuses may be used with one or more plaque disclosing dyes. Plaque disclosing dyes may work by changing the color of dental biofilm and may provide a contrast between the biofilms and tooth surface. Biofilms may retain large number of dye substances due to the interaction—the polarity difference between the components of the dye and biofilm. Electrostatic interactions (proteins) and hydrogen bonds (polysaccharides) bind the particles together. Surfaces which are biofilm free can be easily rinsed off from discoloration, and surfaces which have biofilms requires the removal of biofilm to get rid of the dye.

Figures 19A, 19B, 19C:
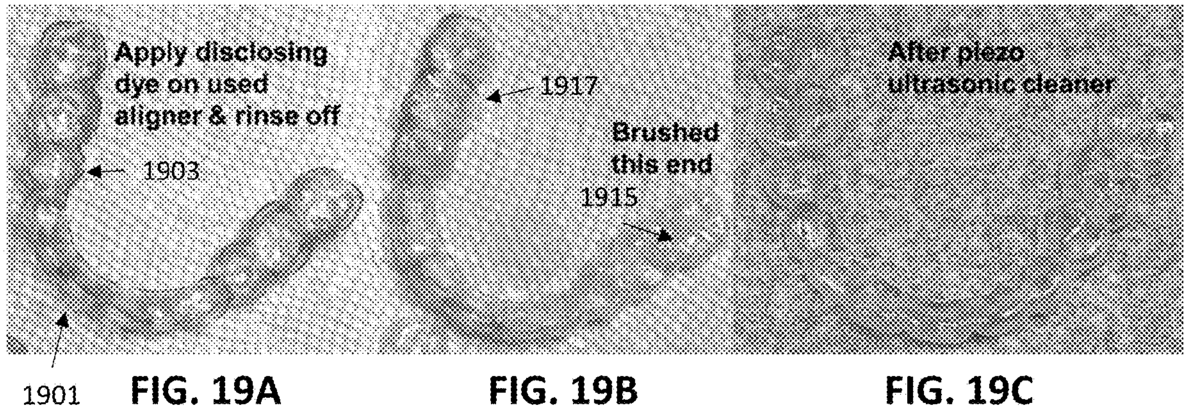
FIGS. 19A-19C illustrates the use of a marker (e.g., dye) for detecting bacteria and/or bacterial byproducts (e.g., biofilm) on a dental appliance that may be used as part of or in conjunction with any of the apparatuses described herein.

For example, FIG. 19A-19C illustrates the use of a dye to detect a biofilm on a dental appliance. In this example, the apparatus, which may be a cleaning apparatus as descried above, such as an ultrasonic cleaning apparatus, may include an indicator (e.g., dye) that may disclose the presence of bacterial biofilm on the appliance. In FIG. 19A, a dental appliance is shown with a dye that may be applied to the appliance. For example, the cleaning apparatus may include a reservoir of dye that may be applied (or diluted and applied) to an appliance inserted into the apparatus. In FIG. 19A, the apparatus 1901 is shown with the dye applied, then rinsed, showing a residual color 1903 staining from the dye. The dye will be more intensely stained in regions in which the bacteria and/or biofilm is more concentrated. The apparatus may detect the staining from all or a region of the device, e.g., by including one or more sensors, such as color-sensors, when applying light (e.g., white light) on or through the appliance. Alternatively or additionally, the user may view the stained appliance to confirm the need for cleaning.

FIG. 19B shows an example of an appliance that has been stained using a dye in which one end 1915 of the appliance has been manually cleaned, e.g., by brushing, showing removal of the dye (and therefore cleaning of the bacteria/biofilm) from this end of the device. The opposite end 1917 remains dyed. For comparison, FIG. 19C shows the same aligner after ultrasonic cleaning using the apparatus describe above. In this example, the apparatus may optically sense the presence of the dye and may continue cleaning until it falls below an appropriate threshold.

Figure 20A:
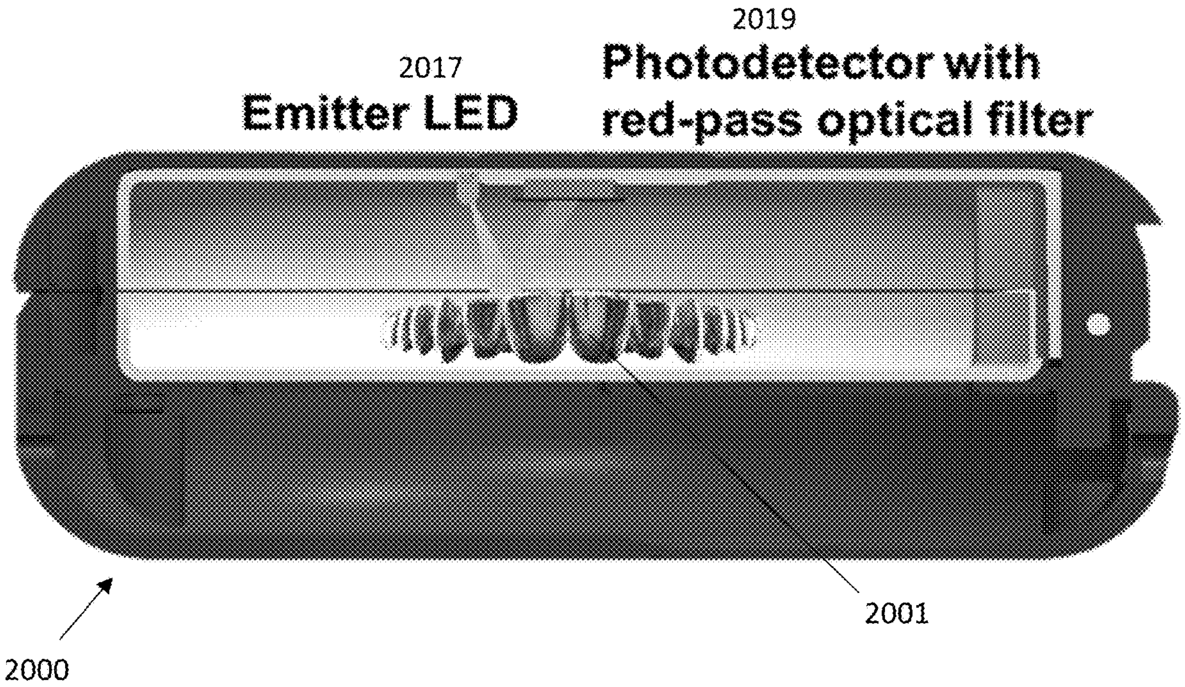
FIGS. 20A-20B illustrate examples of cleaning apparatuses configured to sense or detect bacteria or bacterial byproducts (e.g., biofilm) on a dental appliance; these apparatuses may optionally also be configured to clean the dental appliance.
Figure 20B:
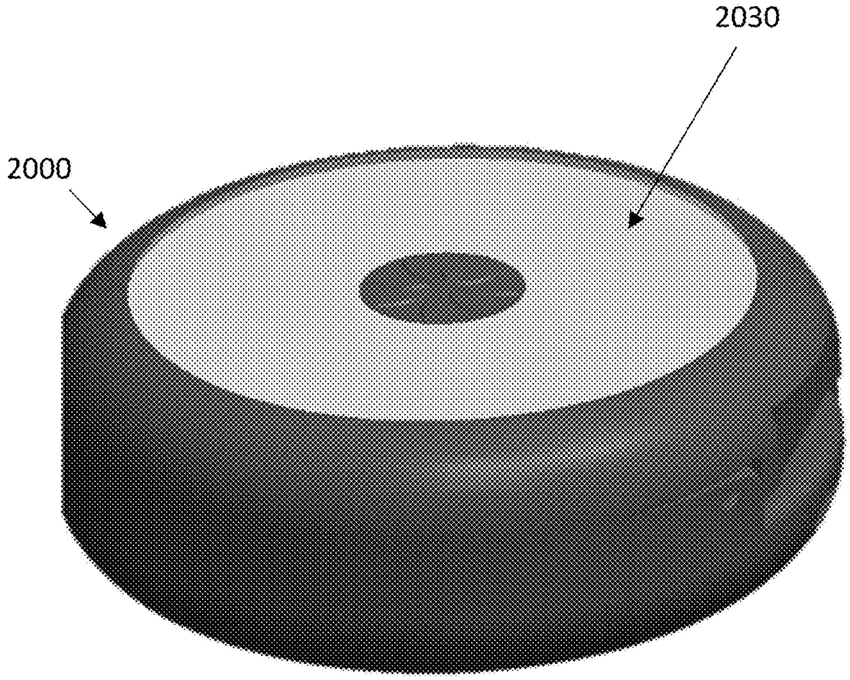

FIGS. 20A-20B illustrate another example of an apparatus 2000 with an integrated optical sensing to detect the likelihood of bacteria, plaque and/or caries. Any of these apparatuses may be configured for direct attachment to dental appliance (e.g., aligner). In some examples the apparatus 2000 may include a removable module with mechanical fitting to couple to the aligner 2001. In this example an optical sensing module includes an emitter 2017 and a detector 2019 with filter (e.g., red-pass filter) similar to the example shown in FIG. 18. Thus, any of these apparatuses may be integrated into a sanitizing apparatus and/or ultrasonic cleaning apparatus.

Alternatively or additionally, any of these sensors may be included as part of the dental appliance. For example, a QLF sensing module can be a miniaturized module that contains optical emitter and receiver, MCU, wireless transmission components and battery etc. A QLF sensing module can be permanently attached to an aligner where plaque formation deemed as a high-risk region. Bonding methods can be adhesive, laser welding, ultrasound welding etc. This design allows for continuous plaque detection yet only on the localized tooth surface.

A QLF sensing module can be designed and fabricated as a removable attachment to an aligner. In such cases, both the QLF module and the aligners shall have mechanical fitting features for positioning, alignment, and attaching. The mechanical fitting features can be snap-fit, sliding rail, twist groove, self-locking pocket etc. The QLF removable module may have a universal interface that is adaptable to different placements along the arch (i.e. buccal, lingual, and occlusal, posterior surface)

As mentioned above and illustrated in FIGS. 20A-20B, QLF sensing can be adapted into any of the sanitizing apparatuses (e.g., ultrasonic cleaning apparatuses) described herein as a non-invasive and indirect sensing modality to detect biofilm residues on a dental appliance. The illumination light source intensity and placement may be configured to provide full coverage for an appliance (e.g., aligner) when placed inside the case in any orientation, or in a predetermined orientation (e.g., when held in a holder). An apparatus with an integrated QLF sensor module may have an optical viewing window 2030 (see, e.g., FIG. 20B) which contains an optical filter that allows emission red florescence to be captured and filters out blue-violet excitation lights. The apparatus may be configured so that the user may see a fluorescence response on the aligners via the optical window if plaque is present. This may provide instant visual feedback of biofilm and plaque build-up and/or may also be a positive indication of the sanitizing and ultrasonic cleaning stations as a comparison from before and after cleaning. As mentioned, in any of these apparatuses the signal form the QLF module may be used as control feedback to the apparatus, to continue, end or repeat a cleaning procedure, and/or to flag a user that further cleaning is or is not necessary.

As mentioned above, a pH sensor may be included in the apparatus. In some examples, an intra-oral pH sensor may be included in the dental appliance itself.

Any of these apparatuses may also or alternatively include a plaque-disclosing dye that can be provided as an optional agent for ultrasonic cleaning. The dye may be made from a vegetable dye, such as Phloxine B, and is safe for oral contact. Two-tone plaque disclosing dye may be used and can differentiate between new and old biofilm (usually pink and blue). Three-tone plaque disclosing solution can identify new, old, and acid-producing biofilms. The discoloration mechanism relies on the reaction of dye substance to biofilm. When a dental appliance is in contact with the dye, discoloration indicates the presence of biofilm; otherwise the dyne does not cause discoloration on clean aligners. To remove discoloration on an aligner, the residue biofilm may be removed and rinsed off.

Disclosing dye can be used in an apparatus reservoir (e.g., an ultrasonic cleaner tank) for dye distribution in the format of either liquid or solid tablets. The container may be made of stainless steel and/or may be resistant of the dye. In apparatuses including ultrasonic cleaning, the ultrasonic vibration of the device offers good distribution of the dye onto an aligner. When the dental appliance is being cleaned in an ultrasonic apparatus with optical viewing window, the user can have direct visual feedback and affirmation of the cleanness. Alternatively or additionally, any of these apparatuses may include a camera of sensor, such as but not limited to: intra-oral dental cameras or the like.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of cleaning one or more dental appliances, the method comprising:

placing the one or more dental appliances on a frame in a chamber of a cleaning case, wherein the frame has a planar shape with a plurality of openings and is in direct contact with a bottom reflective surface of the chamber, wherein the frame elevates the one or more dental appliances from the bottom reflective surface to create a gap between the one or more dental appliances and the bottom reflective surface;

closing a lid of the cleaning case; and activating a cleaning cycle using a controller of the cleaning case, wherein activating the cleaning cycle comprises:

emitting visible light between 400-470 nm from one or more visible light emitting light sources within the closed chamber; and reflecting light from one or more surfaces of the closed chamber, including the reflective bottom surface, to illuminate the one or more dental appliances within the chamber with the 400-470 nm light.

2. The method of claim 1, further comprising continuing the cleaning cycle until one or more of: a timer has counted to a predetermined cycle time, or a stop command has been received by the controller.

3. The method of claim 2, wherein continuing the cleaning cycle until the timer has counted to the predetermined cycle time comprises continuing until the timer has counted to a time that is 3 hours or longer.

4. The method of claim 1, further comprising filling the chamber with liquid prior to starting the cleaning cycle.

5. The method of claim 1, wherein activating the cleaning cycle comprises emitting ultrasound from one or more ultrasound transducers into the chamber.

6. The method of claim 5, wherein emitting the ultrasound further comprises causing cavitation of a fluid within the chamber.

7. The method of claim 1, wherein emitting the visible light between 400-470 nm comprises emitting light at 10 $J/cm^2$ or greater.

8. The method of claim 1, further comprising heating the chamber during the cleaning cycle.

9. The method of claim 1, further comprising sensing a pathogen or a pathogen byproduct on the one or more dental appliances within the chamber.

10. The method of claim 9, further comprising modifying the cleaning cycle based on the sensed pathogen or the sensed pathogen byproduct.

11. The method of claim 1, wherein the bottom reflective surface is flat.

12. The method of claim 1, wherein the frame is a mesh structure.

13. The method of claim 1, wherein the frame is removably positioned on the bottom reflective surface.

14. The method of claim 1, wherein a height of the gap is defined by a height of the frame.

15. A method of cleaning one or more dental appliances, the method comprising:

activating a cleaning cycle of a cleaning case, wherein the cleaning case includes a chamber with the one or more dental appliances therein, wherein activating the cleaning cycle comprises:

emitting visible light between 400-470 nm from one or more visible light emitting light sources within the chamber;

reflecting light from one or more surfaces of the closed chamber to illuminate the one or more dental appliances within the chamber with the 400-470 nm light; and delivering ultrasound energy to the chamber from one or more ultrasound transducers.

16. The method of claim 15, wherein activating the cleaning cycle further comprises heating a fluid within the chamber.

17. The method of claim 15, wherein emitting the visible light comprises emitting light at 10 $J/cm^2$ or greater.

18. The method of claim 15, further comprising continuing the cleaning cycle until one or more of: a timer has counted to a predetermined cycle time, or a stop command has been received by a controller.

19. The method of claim 15, further comprising heating the chamber during the cleaning cycle.

20. The method of claim 15, further comprising sensing a pathogen or a pathogen byproduct on the one or more dental appliances within the chamber.

21. The method of claim 20, further comprising modifying the cleaning cycle based on the sensed pathogen or the sensed pathogen byproduct.

22. A method of cleaning one or more dental appliances, the method comprising:

detecting that a lid of a cleaning case has been closed, wherein a chamber of the cleaning case includes the one or more dental appliances;

activating a cleaning cycle, wherein activating the cleaning cycle comprises:

emitting visible light between 400-470 nm from one or more visible light emitting light sources within the chamber; and reflecting light from one or more surfaces of the closed chamber to illuminate the one or more dental appliances within the chamber with the 400-470 nm light, wherein the one or more dental appliances are removably positioned on a frame in the chamber, the frame having a planar shape with a plurality of openings and being in direct contact with a bottom reflective surface of the chamber, wherein the frame elevates the one or more dental appliances from the bottom reflective surface to create a gap between the one or more dental appliances and the bottom reflective surface; and deactivating the clean cycle when an event occurs.

23. The method of claim 22, wherein the event comprises:

detecting that the lid has been opened, a timer has counted to a predetermined cycle time, or a stop command has been received.

24. The method of claim 22, wherein activating the cleaning cycle further comprises delivering ultrasound energy to the chamber from one or more ultrasound transducers.

25. The method of claim 24, wherein delivering the ultrasound energy comprises causing the one or more ultrasound transducers to emit ultrasound energy of between about 40-45 KHz.

26. The method of claim 22, wherein activating the cleaning cycle further comprises heating a fluid within the chamber.

27. The method of claim 22, further comprising detecting one or more biomarkers for one or more pathogens within the chamber.

28. The method of claim 27, further comprising modifying the cleaning cycle based on a level of the detected one or more biomarkers.

29. The method of claim 22, wherein emitting the visible light comprises emitting light at 10 $J/cm^2$ or greater.

30. The method of claim 22, wherein the frame is removably positioned on the bottom reflective surface.

* * * * *